US012214259B2

(12) United States Patent
Oren

(10) Patent No.: US 12,214,259 B2
(45) Date of Patent: *Feb. 4, 2025

(54) SYSTEMS AND METHODS FOR THE PRODUCTION, MANAGEMENT, SYNDICATION AND DISTRIBUTION OF DIGITAL ASSETS THROUGH A NETWORK IN A MICRO-SUBSCRIPTION-BASED PLATFORM

(71) Applicant: Peloton Interactive, Inc., New York, NY (US)

(72) Inventor: Shachar Oren, New York, NY (US)

(73) Assignee: Peloton Interactive, Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/145,276

(22) Filed: Dec. 22, 2022

(65) Prior Publication Data

US 2023/0128134 A1     Apr. 27, 2023

Related U.S. Application Data

(63) Continuation of application No. 16/359,969, filed on Mar. 20, 2019, now Pat. No. 11,534,661.

(Continued)

(51) Int. Cl.
*A63B 24/00*     (2006.01)
*A63B 21/22*     (2006.01)
(Continued)

(52) U.S. Cl.
CPC ........ *A63B 24/0075* (2013.01); *A63B 21/225* (2013.01); *A63B 22/0605* (2013.01);
(Continued)

(58) Field of Classification Search
None
See application file for complete search history.

(56) References Cited

U.S. PATENT DOCUMENTS

| 5,715,403 A | 2/1998 | Stefik |
| 5,806,071 A | 9/1998 | Balderrama |

(Continued)

OTHER PUBLICATIONS

European Examination Report mailed Sep. 18, 2023 for the European Application No. 19718004.5.

(Continued)

*Primary Examiner* — Jefferey F Harold
*Assistant Examiner* — Charles N Hicks
(74) *Attorney, Agent, or Firm* — AMPACC Law Group, PLLC

(57) ABSTRACT

Systems and methods are for production, management, syndication and distribution of digital assets through a network such as the Internet or wireless network. Digital media assets are distributed to consumers through a syndicated network of Outlets under control of a central platform. Distribution is format agnostic. There is a single platform between the B2B2C, wherein a platform allows, through a single access for each stakeholder, the ability to each have control over availability dates and pricing specifications to a plurality of merchants and/or subscription outlets or channels. Subscription channels can support micro-subscriptions with diversely curated and priced offerings, including acceptance of crypto-currency. The delivered media assets may include content associated with an exercise apparatus, including content for an exercise session including computer generated content and computer augmented content created in response to exercise session data.

20 Claims, 23 Drawing Sheets

Related U.S. Application Data

(60) Provisional application No. 62/646,273, filed on Mar. 21, 2018.

(51) Int. Cl.

| | | |
|---|---|---|
| *A63B 22/06* | (2006.01) | |
| *A63B 71/06* | (2006.01) | |
| *G06N 3/08* | (2023.01) | |
| *G06Q 20/12* | (2012.01) | |
| *G06Q 20/36* | (2012.01) | |
| *G06Q 40/04* | (2012.01) | |
| *G16H 20/30* | (2018.01) | |
| *G16H 40/60* | (2018.01) | |
| *H04N 21/4627* | (2011.01) | |
| *H04N 21/472* | (2011.01) | |
| *A63B 21/005* | (2006.01) | |

(52) U.S. Cl.
 CPC ...... *A63B 24/0059* (2013.01); *A63B 24/0084* (2013.01); *A63B 24/0087* (2013.01); *A63B 71/0622* (2013.01); *G06N 3/08* (2013.01); *G06Q 20/1235* (2013.01); *G06Q 20/3672* (2013.01); *G06Q 40/04* (2013.01); *G16H 20/30* (2018.01); *G16H 40/60* (2018.01); *H04N 21/4627* (2013.01); *H04N 21/47202* (2013.01); *A63B 21/0051* (2013.01); *A63B 2024/0025* (2013.01); *A63B 2024/0068* (2013.01); *A63B 2024/0081* (2013.01); *A63B 2024/0093* (2013.01); *A63B 2024/0096* (2013.01); *A63B 2071/0625* (2013.01); *A63B 2071/065* (2013.01); *A63B 2071/068* (2013.01); *A63B 2220/10* (2013.01); *A63B 2220/20* (2013.01); *A63B 2220/30* (2013.01); *A63B 2220/51* (2013.01); *A63B 2220/72* (2013.01); *A63B 2220/806* (2013.01); *A63B 2220/808* (2013.01); *A63B 2225/50* (2013.01); *A63B 2230/06* (2013.01); *A63B 2230/062* (2013.01); *A63B 2230/75* (2013.01)

(56) References Cited

U.S. PATENT DOCUMENTS

| | | |
|---|---|---|
| 5,892,535 A | 4/1999 | Allen |
| 5,893,110 A | 4/1999 | Weber |
| 5,920,700 A | 6/1999 | Gordon |
| 6,389,541 B1 | 5/2002 | Patterson |
| 6,477,508 B1 | 11/2002 | Lazar et al. |
| 6,502,102 B1 | 12/2002 | Haswell et al. |
| 6,665,797 B1 | 12/2003 | Keung |
| 6,684,248 B1 | 1/2004 | Janacek et al. |
| 6,751,670 B1 | 6/2004 | Patterson |
| 6,799,165 B1 | 9/2004 | Boesjes |
| 6,824,051 B2 | 11/2004 | Reddy |
| 6,925,469 B2 | 8/2005 | Headings |
| 6,947,959 B1 | 9/2005 | Gill |
| 7,043,051 B2 | 5/2006 | Kuzmich |
| 7,089,309 B2 | 8/2006 | Ramaley |
| 7,110,984 B1 | 9/2006 | Spagna et al. |
| 7,209,892 B1 | 4/2007 | Galuten et al. |
| 7,346,687 B2 | 3/2008 | Lipscomb |
| 7,469,230 B2 | 12/2008 | Vaidyanathan |
| 11,534,661 B2 * | 12/2022 | Oren .............. G16H 40/60 |
| 2002/0026581 A1 | 2/2002 | Matsuyama |
| 2002/0083006 A1 | 6/2002 | Headings |
| 2002/0138619 A1 | 9/2002 | Ramaley |
| 2003/0083948 A1 | 5/2003 | Rodriguez |
| 2004/0193902 A1 | 9/2004 | Vogler et al. |
| 2006/0173761 A1 | 8/2006 | Costakis |
| 2006/0190290 A1 | 8/2006 | Gomez |
| 2009/0106110 A1 * | 4/2009 | Stannard .......... G06F 16/178 |
| | | 705/14.1 |
| 2010/0089224 A1 | 4/2010 | Fratti et al. |
| 2012/0264570 A1 | 10/2012 | Watterson et al. |
| 2012/0266201 A1 * | 10/2012 | Kanojia ......... H04N 21/25841 |
| | | 725/109 |
| 2013/0347025 A1 * | 12/2013 | Prakash ......... H04N 21/25875 |
| | | 725/25 |
| 2014/0038781 A1 | 2/2014 | Paul |
| 2016/0357514 A1 | 12/2016 | Riggs-Zeigen |
| 2017/0046503 A1 | 2/2017 | Cho et al. |
| 2018/0056132 A1 | 3/2018 | Foley |

OTHER PUBLICATIONS

Notice of acceptance for patent application dated Jul. 9, 2024 for Australian Patent Application No. 2019240387.

* cited by examiner

SYSTEMS AND METHODS FOR THE PRODUCTION, MANAGEMENT, SYNDICATION AND DISTRIBUTION OF DIGITAL ASSETS THROUGH A NETWORK IN A MICRO-SUBSCRIPTION-BASED PLATFORM

CROSS-REFERENCE TO RELATED APPLICATIONS

This application is a continuation of U.S. patent application Ser. No. 16/359,969 filed Mar. 20, 2019, now U.S. patent Ser. No. 11/534,661, which claims the benefit of or priority to U.S. Provisional Patent Application No. 62/646,273, filed on Mar. 21, 2018 entitled "SYSTEMS AND METHODS FOR THE PRODUCTION, MANAGEMENT, SYNDICATION AND DISTRIBUTION OF DIGITAL ASSETS THROUGH A NETWORK IN A MICRO-SUBSCRIPTION-BASED PLATFORM," and is related to U.S. Pat. No. 7,693,914 issued on Apr. 6, 2010 entitled "SYSTEMS AND METHODS FOR THE PRODUCTION, MANAGEMENT, SYNDICATION AND DISTRIBUTION OF DIGITAL ASSETS THROUGH A NETWORK," which are hereby incorporated by reference in their entirety.

BACKGROUND

The disclosure generally relates to the field of production, management, syndication and distribution of digital assets, and more particularly to systems and methods for the production, management, syndication and distribution of digital assets through a network of outlets which further distribute the assets to end users.

A digital asset (also referred to as a "media asset") includes electronically formatted content that contains digital data. A digital asset may include an electronic file containing digital data such as audio, video, audio-video, multimedia, music, graphics, or any other type of media-related content. Digital assets may be stored and/or embodied in a variety of electronic formats. For example, an audio or music file can be stored as a WA V or a WMA-type format. As another example, a digital asset can be a promotional file or a download that a recording company or musical group produces or creates. As a further example, a digital asset may include digital content generated and/or streamed live to a user.

Digital assets are often managed through one or more servers accessible via a network such as the Internet or a wireless network. A content owner such as a recording company may transmit a digital asset to another party (e.g., an end user) in a limited number of electronic formats through one or more service providers or systems which each may specialize in one or a limited number of electronic format(s). The content owner may also have an interest in controlling and monetizing the distribution and use of the digital assets. To support and manage many or all of the potential electronic file formats in which a digital asset can be stored and transmitted, requires the content owner, or an associated host server or service provider, to possess a relatively large amount of processing and/or storage capacity, as well as proper management software logic and systems to handle a wide range of electronic file formats and financial arrangements. Typically, this amount of processing and/or storage capacity is very expensive and time consuming to maintain. Furthermore, the aggregation of all relevant skills and capabilities in one unified distribution system is non-existent. There exists a need for systems and methods for limiting the amount of processing and/or storage capacity needed for handling and distributing digital assets to consumers through the Internet or a wireless network. Furthermore, there exists a need for systems and methods for improving the operational efficiencies involved in the process of syndicating digital media assets to a distribution network and to end-users or consumers.

At least one system and method has been designed for controlling the use and distribution of digital works. However, this conventional system and method does not disclose how to handle a wide range of file formats available to network users. This conventional system and method lacks a database for metafiles in support of various digital works and in support of the association of such digital works with each other when the metafiles dictate such association or grouping. Therefore, a need exists for systems and methods for the handling and distribution of digital assets through a network such as the Internet or a wireless network in a wide range of electronic file formats.

While this conventional system and method may be able to control and distribute digital works in some file formats over a network, the files that are controlled and distributed by the disclosure are always related to a fee, a fee description, or an e-commerce transaction. A fee, fee description, or e-commerce transaction is not always required for handling and distribution of digital assets. Therefore, a need exists for systems and methods for handling and distribution of digital assets unrelated to a fee through a network such as the Internet or a wireless network.

The conventional systems and methods described above are limited to document publishing and digital rights management. Document publishing typically involves a printer or a printer module. The digital rights management relies primarily upon the consummation of an e-commerce transaction for digital works, specifically music or other electronic files that are purchased for or otherwise accessible after payment of a fee.

Moreover, these conventional systems and methods lack any efficient reporting feature or mechanism for providing reports. Although this system and method disclose a credit database, it lacks any reporting derived from a report database and metafiles in support of a syndicated digital work. Thus, using a conventional system and method, content providers would lack efficient management in the distribution of digital assets, and further lack focus in their marketing efforts for their digital assets. There exists a need for systems and methods for management and reporting in the distribution of digital assets through a network such as the Internet or wireless networks.

One present model for distribution of digital assets is that of the "digital service provider" ("DSP"). The focus of the DSPs is licensing and sub-licensing of digital content owned by the digital content owner(s). They license and aggregate content or digital assets from owner(s) of digital content and distribute this content by sale or license of the digital asset to end-user(s). This may be done, for example, by the licensing of individual digital item(s) or by means of subscription allowing the end-user(s) to have access to predetermined digital content for a fixed period of time.

One of the methods by which this distribution is protected from being used without authorization is by encryption of the content. The user requires a "key" to decrypt the digital information and this "key" is provided to the user with the license. This method of distribution works well for certain business purposes (e.g., generation of revenue from specific type(s) of digital content). However, since these DSPs are set up to distribute only specific type(s) of digital content form which they can derive licensing revenue, these DSPs may not be able to perform all of the business functions desired by the content owner(s). For example, each piece of revenue-generating digital content (e.g., a particular track of audio) may be associated with numerous other digital material(s) in various formats, some of which may be helpful to the content owner in marketing and/or promoting the revenue-generating digital content.

For example, this promotional content may include videos, screen savers, material(s) relating to the artist(s) involved in the digital content, etc. It also may include right(s) to play revenue-generating content for a limited amount of time. The owner(s) of the digital content may wish to have this promotional distribution to be as widespread as possible without directly generating revenue(s) from such distribution. Present DSPs are ill-suited for performing this function. Their systems typically support only distribution of a limited number of type(s) of electronic files (e.g., audio or video in one or more selected formats).

Moreover, since their digital file distribution capabilities are limited, they are also limited in the amount of information they can collect and/or send back to the content owner relating to, for example, the demographics of the distribution of all of the digital content, including promotional content and not merely the revenue-producing content. There is a need, therefore, for a system which can direct distribution of all digital content relating to a particular folder, or project, of the owner(s) of the digital content in a "format agnostic" manner (i.e., no format limitation(s)). There is also the need to have the capability to collect data regarding the demographics of the distribution of each of these type(s) of file(s) in a folder relating to a project on an individual basis.

Moreover, there is a need to collect all of these capabilities into one integrated system so that the owner(s) of the digital content can have one entity attend to its entire requirement for digital distribution and information collection relating to that distribution. Another category of service providers offers asset distribution to a network of web sites. These service providers rarely offer the ability to customize the user experience involved in the delivery of media assets to end-users on a per-website basis for the distribution network members. Some service providers offer limited functionality related to this need. For example, they may allow a credit line and logo and some visuals related to each specific outlet to be shown in relation to the user experience. Such elements are normally featured within a pre-designed user interface environment.

There is a need, therefore, for a system and method that both allow member sites in the distribution network to control a variety of user interface elements pertaining to the assets they use via the service, as well as allow content owners similar controls over user interface element relevant to their asset(s).

In light of the above, there exists a need for systems and methods for the production, management, syndication and distribution of digital assets through a network such as the Internet or wireless networks.

At least one system and method has been designed for controlling the delivery and resulting billing in a digital distribution workflow. However, this conventional system relies on trading with a normal currency. Therefore, this conventional system lacks the ability to accommodate secure long-term holding of the potential discount value of a service by a subscriber, nor facilitating pre-payment by a subscriber to a favorite content creator that would fund several years of the content creator's work while reducing or eliminating risk for the subscriber.

SUMMARY

Systems and methods of the present disclosure include systems, methods and use cases related to the curation of digital assets into unique micro-subscriptions, each with its own echo-system, term period and subscriber terms-of-service. The disclosure enables end-users to subscribe for the right to access, listen to and view content in specific micro-subscription echo-systems which have been provisioned, curated and priced by content owners, brands and merchants, echoing and expanding on B2B2C (business-to-business-to-consumer) workflows articulated in U.S. Pat. No. 7,693,914, which establishes a unique operational workflow between content owners, merchant outlet(s), and consumers (or in the case of subscription offering, "subscribers"), all in one, efficient Platform.

While on-demand subscription services have grown in popularity in recent years, the model is problematic for several stakeholders, namely content creators and subscribers. For example, in music, while full-catalog music brands keep emerging in the marketplace, and while record companies receive a lion share of the revenue generated by such subscriptions, many established artists and many music fans are not being properly served by the current model.

Digital files are normally transmitted under a subscription in a 1-to-1 relationship, where a specific merchant outlet has aggregated select catalogs to be provisioned under a specific price, representing one subscription merchant outlet entity. The subscription price thus unlocks the available catalogs under the one merchant outlet. While this has become a known standard, the model is inherently problematic for the individual owners and creators of the catalog since the per-play revenue they receive within such a subscription has been publicly known to be very low as compared to artists' past recorded music revenue. For example, where an establish artist used to sell significant volumes of a new album at a significant retail price, the same artist has seen that recorded music revenue replaced by getting paid a fraction of a cent per song play in prevailing subscription models, which has significantly diminished the artist's income from recorded music.

In addition, the conventional pricing of the so-called "full catalog" offerings (e.g., at $9.99 a month in the USA) proves expensive for some subscribers, while including more than they need to subscribe to. Indeed, if all a subscriber likes to listen to is country music, they are still paying for all genres, with access to the tune of 50 MM to 60 MM tracks they don't really need. For context, an average music subscriber would listen to only 250-1,200 songs a month, and often these are the same songs from the same favorite artists. Therefore, a service that enables subscribers to only pay for the music and artists they want would prove advantageous for subscribers. Such a service can also increase the recorded music revenue for artists and their label imprints as compared to the revenue they receive from all-catalog services. For example, if an artist charges $1 per month for their dedicated streaming channel, it is the equivalent of a 10% market share in leading all-catalog $9.99 per month services. No one artist would normally receive such revenue per subscriber from all-catalog merchant outlets. In addition, a label/imprint that specialized in a specific sub-genre and can price their own micro-subscription at, for example, $2.99 a month, would never see that equivalent (30% market share through all-catalog services) through standard distribution systems.

To the extent that certain merchant outlets have devised the notion that micro-subscriptions is a business model worth pursuing, they have faced numerous challenges in conceptualizing a successful and scalable model. For one, large and market leading content providers submit their catalogs through a technical supply chain in a unified manner, so the merchant outlets received each product with a unified price, without a means by which instructions about micro-channel placement and pricing could be more granular. Second, merchant outlets tend to support one unified subscriber interface—which in the case of on-demand streaming normally involves a mobile application—without regard to the unique curating, pricing and merchandising needs of any specific micro-subscription offering, and importantly, how its activity is tracked and properly reported and paid for on the back-end to stakeholders. Indeed, micro-channel merchant outlets have normally focused on one, singular micro-channel with one user-experience and mobile application. In other cases, attention was given to user-generated channels (meaning the content is not licensed from and delivered by the content owner supply chain but is rather uploaded by end-users), without further flexibility to offer other curation concepts such as cross-label genre channels, themed channels and playlist channels, to name a few.

This limitation of delivery pathways and methods has created several business challenges in the marketplace, which the present disclosure aims to resolve. By improving on inventor's original U.S. Pat. No. 7,693,914 with this filing, a system and method is created which streamlines the administration, production, syndication and monetization of micro-channel subscription plans in a uniquely novel, efficient and scalable manner. The improvements provided by present disclosure have been conceived with the efficiencies enumerated above, and also with the attention to how the embodiments of the present disclosure patent resolve challenges to multiple stakeholders.

By allowing content owners to either independently or by joining together curate subscription experiences that target specific core subscribers with unique offerings relevant to catalog curation, subscription duration, and subscription price, content owners stand to improve their per-subscriber revenue. This proposition is shown as true for artists and for label imprints and can also drive growth for content owner's central offices with the concept being additive in nature. Most subscribers over time may subscribe to 3-4 micro-channels at a time, which may result in their total monthly spending being higher than $10. Furthermore, the merchant outlet's ability to deliver the unique subscription benefit to the right target audience improves through the ability to tailor marketing for a specific segment. This has been proven in some ways via OTT video services whereby subscribers can "cut the cord" and pay HBO, Netflix and other TV services for their unique subscriptions. However, in those cases, in order to view multiple studios' work today, the subscriber must download and install and subscribe on each branded app separately. By contrast, an embodiment of the patent present disclosure relates to multiple, and indeed unlimited, number of micro-subscriptions (or "channels") being available for individual subscription, and served via a central and unified OTT app, using one set of credentials across allmicro-subscriptions.

At least one system and method has been designed to facilitate crowd-funding for content creators. However, such systems involve cash contributions, and therefore the horizon for project delivery by the content provider is relatively short. Our disclosure, by comparison, can support multiple years of work being pre-funded by core fans with mitigated concern about the multi-year service fees collected and escrowed by the platform to the benefit of content providers, merchant outlets, and subscribers. Therefore, a need exists for systems and methods for the centralized, accurate and holistic administration of a plethora of micro-payment subscription offerings, including such that leverage crypto-currency as a payment method to pre-fund a longer horizon than usual for the content owner.

An additional value-add provided with the support of tradable crypto-currency may be a "fan club" of sorts whereby owning certain crypto-currency class can provide a limited discount period across all, or a certain finite volume of, micro-subscription channels. The value of such a club can easily be recognized by a subscriber who intends to subscribe to enough micro-subscriptions during a period so as to quickly recoup and benefit from the price of the fan club crypto-currency class. With such crypto-currency class being tradable as is the norm in crypto-currency offerings, the market may set higher valuation over time for the price of the fan club. Such secondary crypto-currency class within the envisioned platform can help sponsor platform enhancements.

The disclosure addresses the needs described above. The disclosure provides systems and methods for the production, management, and syndication of the distribution of digital assets through a network of Outlets via the Internet and/or a wireless network. The disclosure provides systems and methods for the handling and distribution of digital assets through a network such as the Internet or a wireless network in a wide range of electronic file formats. Furthermore, the disclosure provides systems and methods for the handling and distribution of digital assets unrelated to a fee through a network such as the Internet or a wireless network. Furthermore, the disclosure provides systems and methods for management and reporting in the distribution of digital assets through a network such as the Internet or wireless networks. Moreover, the disclosure provides systems and methods for the project-centric management of the syndication and distribution process for various media assets (free or for sale) in ways that address and compliment the business needs of both content owners and Outlets.

Generally described, the systems and methods according to a preferred embodiment of the disclosure are for the production, management, and syndication of the distribution of digital assets through a network of outlets via the Internet and/or wireless telecommunication networks. More specifically, the systems and methods according to a preferred embodiment of the disclosure are for the project-centric production, management, syndication and distribution of various assets to a distribution network in a customizable manner that is controlled in some respect by content owners and in some respect by Outlets.

The systems improve efficiencies in the operational processes of production, management, distribution, reporting and analysis of digital assets. Furthermore, the systems are "project-centric" and "format agnostic," and support a large variety of different types of digital assets. The systems provide publishing and distribution logic that provides the ability to download, stream, handle or otherwise accommodate digital asset on a project-centric basis, regardless of the type of asset. The system scan handle files for delivery via the Internet including, but not limited to, Microsoft WMA, Microsoft WMA streaming clips, WMV (video), e-cards, flash cards, screen savers, MP3, AAC, aacPlus, Ogg Vorbis, FLAC, MQA, and/or other Internet delivery files. Furthermore, the systems can handle files for delivery via a telecommunications device communicating via a network such as a wireless network, including, but not limited to, VOX streams, MIDI ring tones, Java audio and video, Internet files, telecom-specific files, and wireless device specific files. This feature permits the systems to accommodate a variety of partner and client business models in support of both Internet delivery and telecommunication media asset delivery. Finally, the systems provide enhanced reporting capabilities on the usage of the digital assets handled by the disclosure.

More particularly described, the systems allow one or more owners or managers of a digital work to securely and efficiently distribute and administer the use of the digital work to multiple business partners (so-called Distribution Network, or Outlets) and ultimately to the consumers of such businesses, using computerized networks such as the Internet, a telecom network, a wireless network, or other similar systems.

Such administration includes (i) the posting of a digital work onto the distribution system, (ii) the entry of information related to the digital work in a fashion that is uniquely conducive for efficient administration of the digital work and its related data, (iii) the application of usage rights that are communicated to receiving Outlets and/or to consumers (some of which remain embedded within the uploaded digital work using digital rights management applications from third parties), (iv) the assignment of specific distribution avenues for the digital work, 0.0 whereby selected Outlets are chosen to receive the work throughout the distribution network, and whereby each outlet may have certain unique usage rules specific to the same digital work, and whereby the user interface for the delivery of the digital work to consumers may differ uniquely per Outlet, and (v) the monitoring of activity related to the digital work throughout the distribution life cycle and post end-date, and the generation of analysis data from the system that supports the business needs of the owner or manager of the digital work, as well as the business needs of the Outlets that are members of the distribution network.

The present disclosure features a computer system with an IP database which is updated on a regular basis. When a particular user accesses the system, the user's IP address can be read, and a determination made as to what country the IP address is located based on the information stored in the database. To a lesser extent, the state and/or zip code of the user can also be derived from the IP address. This provides the system with a means for determining whether a territorial restriction is applicable to a particular customer.

The network and infrastructure of the present disclosure, rather than focusing on providing the most efficient form of distribution for a specific format of digital information is focused, instead, on the efficient management and delivery of all type(s) of information, whether it be in digital download format, stream format, or any other format.

The distribution of the multiple file(s) of each project may be handled through a syndication network of outlet(s) which, in turn, supply the file(s) to the end-user(s) in the outlet network. These outlet(s) may be a mix of outlet(s), none of which individually supports all of the media format(s) in the product package. For example, one group of outlets may handle distribution of digital downloads, whereas another outlet or outlets may be used for distribution of audio or video streams.

End-user information may be collected by means of "opt-in" survey(s). When accessing the survey(s), a small window is opened asking for the end-user(s)'s e-mail address. An option is given to the end-user to "opt-in" to the artist(s)'s mailing list, and/or the website's mailing list, and/or another "generic" mailing list. Birthday and other information may also be asked to supply a "generic" demographic record, which can be associated with future downloads to these specific consumer(s). This is valuable information for the content owner(s) in their marketing efforts. The survey(s) can be customized per asset and/or per Outlet.

In the case of encrypted assets, the opt-in survey(s) may be followed with a License Key template that includes the usage rules information and other field metadata. This template can also be customized per asset and/or per Outlet. When encrypted, assets expire (should the usage rules be set to do so), and an expiration notice is displayed for the end-user. This template can also be customized per asset and/or per Outlet.

The improved disclosure addresses the needs described above. The disclosure provides systems and methods for the production, management, syndication, distribution and monetization of digital assets through a network of Outlets through the Internet and/or a wireless network, wherein the digital assets are offered through a plurality of micro-subscription offerings.

The improved disclosure provides systems and methods for using all relevant data from the above process to deliver reports from the clearinghouse to financial accounting systems, customer care systems (CRM), technical reporting systems, sales and royalty reporting systems, quality assurance systems, mid-tier gateway vendors, and any other system designated by Stakeholders such as merchants, mobile operators, ISPs, payment gateways, content owners, publishers, merchant outlets, and other Stakeholders to receive such data in a manner that supports business rules and decision making rules for such Stakeholders.

The improved disclosure improves the consumer experience by providing the operational processes by which content owners, and in turn merchant outlets, can manage the consumer's entitlement to a plurality of subscription offerings, each boasting a uniquely curated experience at a uniquely designed subscription price(s) and period(s). This information can also be used by the relevant Stakeholders to apply a plurality of business rules, practices and policies, as between them and the subscriber or as between the Stakeholders themselves, all relevant to a plurality of subscription model options. One of the novel aspects of the disclosure is a structural platform which can be distributed in a unique way and also support business relationships between all stakeholders contained within one platform as opposed to decoupled and separate platforms. For instance, the improved structural software platform can include micro-subscriptions that curate music catalog from two or more content owners, which together agree on a monthly subscription price, and which then share in the revenue pro-rate to play counts per period.

Since the platform can support an "additive" model of hundreds (and ultimately, unlimited number) of micro-subscriptions, and each micro-subscription contains its own unique echo-system relative to participating content owners and their unique agreement as to how to share revenue from each unique micro-subscription, the system supports the administration of these unique business rules per micro-channel; branding and merchandising the channel according to the guidance or hands-on work of its content providers and/or the merchant outlet accommodated by the micro-channel; and then reporting plays and subscribers to the stakeholders regularly, and remitting the right payments to each.

In addition to the described model supporting a new and novel business solution for music artists and labels, it can equally serve other creative personalities in adjacent content sectors, such as sports, fitness, film and TV. Any person with a reason to engage subscribers for a unique subset of media delivery can leverage the present disclosure to improve its monetization of its assets with its core end users. For example, a fitness instructor can curate unique and exclusive fitness lessons in her/his personally-branded channel and offer it to end users using the embodiment of this novel invention. Another example is a private instructor who customizes private lessons in audio, video and other formats for an individual end user or a subset group of end users can leverage the embodiment of this patent to better maximize business opportunities. In such examples of additional usage sectors, additional input from end users may influence the service provided to the end user by the channel. For example, a stationary exercise bike could deliver end-user exercise performance data to the system which in turn uses such individualized data to modify the set of services (for example, music) provided to the end user by the said channel.

DESCRIPTION OF DISCLOSED EMBODIMENTS

Figure 1:
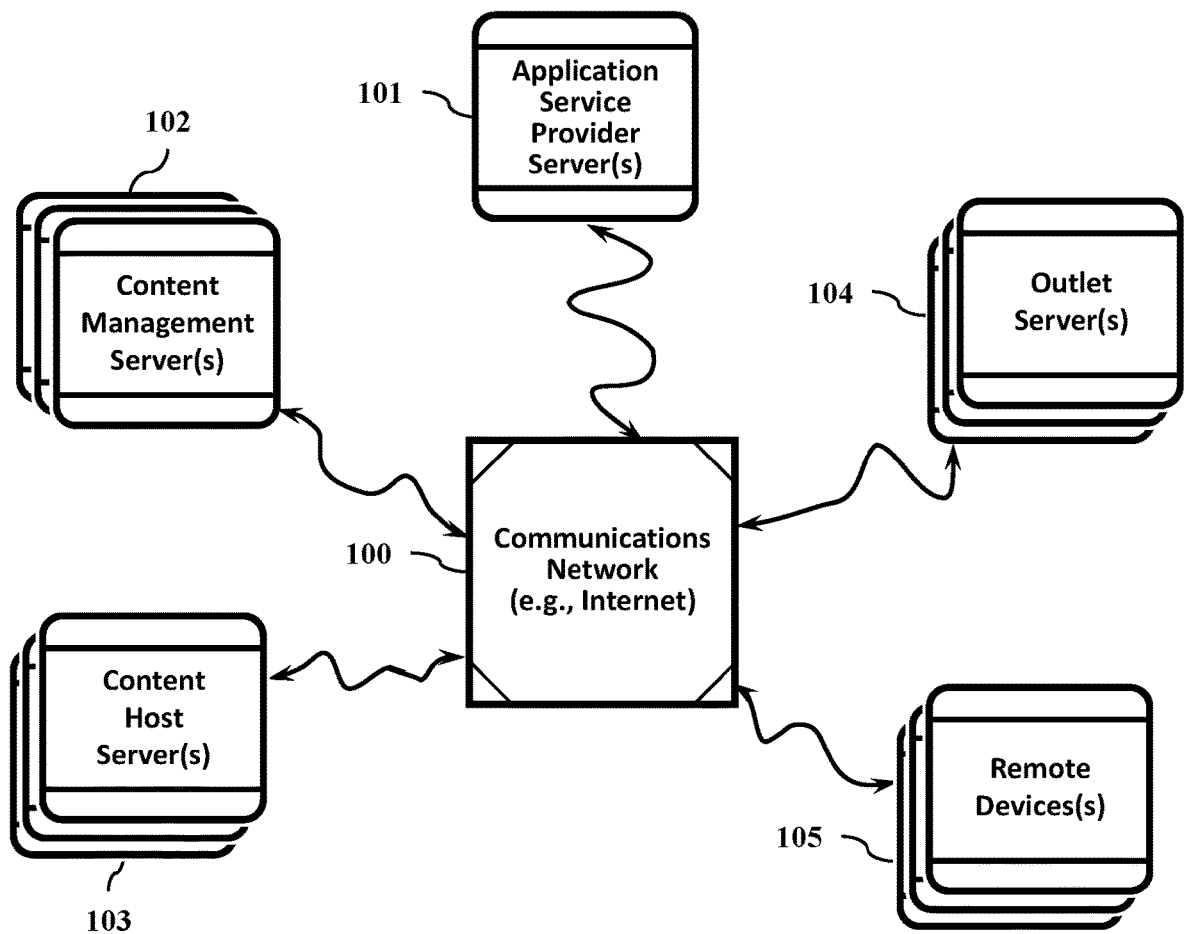
FIG. 1 is a block diagram of a computing environment in which the present disclosure functions according to one embodiment of the present disclosure.

Systems and methods according to embodiments of the disclosure provide for the production, management, syndication and distribution of digital assets through a network such as the Internet and/or a wireless network. The systems and methods allow for efficient use of processing and/or storage capacity for handling and distributing digital assets through the Internet or a wireless network. Further, the systems and methods are for the handling and distribution of digital assets through a network such as the Internet or a wireless network in a wide range of electronic file formats. Furthermore, the systems and methods are for the handling and distribution of digital assets unrelated to a fee through a network such as the Internet or a wireless network. Moreover, the systems and methods are for management and reporting in the distribution of digital assets through a network such as the Internet or wireless network.

In addition, the systems and methods according to an embodiment of the disclosure provide for the unified administration of multiple micro-subscription offerings, which can be grouped through one or more merchant outlets, via web pages or mobile applications, each such micro-subscription curating specific digital assets for unique and specific subscription arrangements. In addition, such subscription enrollment can be attained by e-commerce payment methods, as well as PIN codes, vouchers, and crypto-currencies.

For example, the systems can be used to produce, manage, and distribute digital assets such as promotional files or downloads for a client record company to other media companies such as entertainment portals, retailers, or other related businesses. Furthermore, the systems can be used to provide Licensors and Distributors control over their digital assets and their distribution through a website interface. Finally, the systems can be used to permit Distributors to acquire their own promotional files or other digital assets from Licensors, and further prepare these assets for distribution to a consumer, subscriber or end-user.

As described herein, a "Licensor" includes an entity (also known as content owner) that provides new digital assets such as media files, downloads, and promotions. The Licensor can impose specific user limitations on the content of its digital assets such as the duration of play, number of plays, types of distribution, and quality.

As described in this specification, a "Distributor" includes an online store, online music outlet, a web portal, a connected exercise apparatus, a mobile application, or another entity that distributes digital assets. A Distributor can also be known as an Outlet or a Channel Partner. Typically, a distributor can add a link to an associated website to permit a consumer to purchase products in conjunction with listening, viewing, or otherwise accessing another digital asset such as a promotional prior to purchase.

As described herein, a "Consumer" and a "Subscriber" refer to end-users of the service(s), who consume digital assets via a variety of models such as pay-to-own, rent, subscribe, or obtain a reward. As described herein, a "project" is a folder comprised of several, or multiple "digital works" or digital assets. As described, a "merchant" and "merchant outlet" include one or more of outlets who are in the business of selling media assets, selling subscriptions to media assets, renting out media assets, leveraging media assets as rewards, incentives and promotions, or otherwise exploits media assets in various methods as further defined herein, whereby the merchant is the entity facing the end user, consumer or subscriber who consume the media assets. For example, a merchant can be a retailer, a consumer brand, a fitness company, a mobile carrier, a record company, an artist, or a fitness instructor, just to name a few.

The disclosure includes methods and systems for providing digital assets of one or more content owners to a computer system accessible by consumers. In one embodiment, the system and steps include creating a database of media assets in one or more formats, and organizing the database by project, each project associated with media assets in the database relating to a selected attribute of the asset other than the format of the asset. The content owner may also preset parameters (e.g., responsive to communication from the computer system) relating to media formats, pricing, subscriptions and other product provisions. An outlet database may be created including acceptable media formats, pricing and other product provisions. Responsive parameters can include acceptable media formats, pricing and other product provisions. A consumer may request media assets of a selected project, which may then be transmitted in formats acceptable to the content owner. The media assets of said selected project are transmitted to the computer system of said consumer in a format acceptable to the consumer (or application on the consumer device) selected from the selected media assets.

In some embodiments, methods and systems are provide digital assets of one or more content owners to a computer system of one or more merchant outlets for further distribution to computer systems of consumers associated with said merchant outlets. The system and steps include the steps of: (a) creating a database of media assets in one or more formats, (b) organizing the database by project, each project associated with media assets in the database relating to a selected attribute of said asset; (c) creating an outlet data base including acceptable media formats, pricing, subscription models and other provisions for a merchant outlet subject to preset parameters set by the content owner and merchant outlet relating to media formats, pricing and other product provisions acceptable to said communicating merchant outlet, (d) selecting media assets responsive to parameters controlled by said communicating merchant outlet including acceptable media formats, pricing and other product provisions, and (e) where applicable, affecting, customizing and/or and altering the media, as delivered, based on the real-time data and/or stored data provided by the individual end user and/or end user device(s). There is a responsive communication with a computer system of a consumer of said merchant outlet requesting media assets of a selected project. The said media assets are transmitted to said merchant outlet in formats acceptable to both the content owner and the merchant outlet. The media assets of said selected project are transmitted to the computer system of said consumer in a format acceptable to the consumer selected from the media assets selected in step (d).

Referring now to FIG. 1, an exemplary computing environment in which the present disclosure may be implemented will now be described. The computing environment includes at least one content management server 102, which generally belongs to or is controlled by the entity which creates, owns, and/or is the licensor of the media asset(s) to be distributed. The content and/or related content and data may be hosted in one or more content host servers 103. For example, promotional materials for a record album owned by the content owner may be hosted in the server of the service organization which produced this promotional material on behalf of the content owner.

One or more application service provider (ASP) servers 101 are also provided for hosting a software platform of the present disclosure. Although an application server is shown, it will be appreciated that the software platform may reside on any computing system appropriately linked to the remainder of the system element(s). The computing environment also includes one or more outlet server(s) 104 and remote devices 105. The remote device(s) 105 include end-user computing devices operable to interface with one or more of the outlet syndicate server 104 and may include computer(s), portables (including mobile smart phones), wearables, televisions, smart speakers, or other devices (e.g., automobiles, exercise equipment) to which the media asset(s) may be distributed.

Communications between the various components of the system may take place over a communications network 100, such as the Internet. It will be appreciated, that any communications network (e.g., wired, wireless, cellular, wide area network, local area network) and communications path (e.g., Bluetooth connection) suitable for facilitating communications between the components as described herein may be used.

Figure 2:
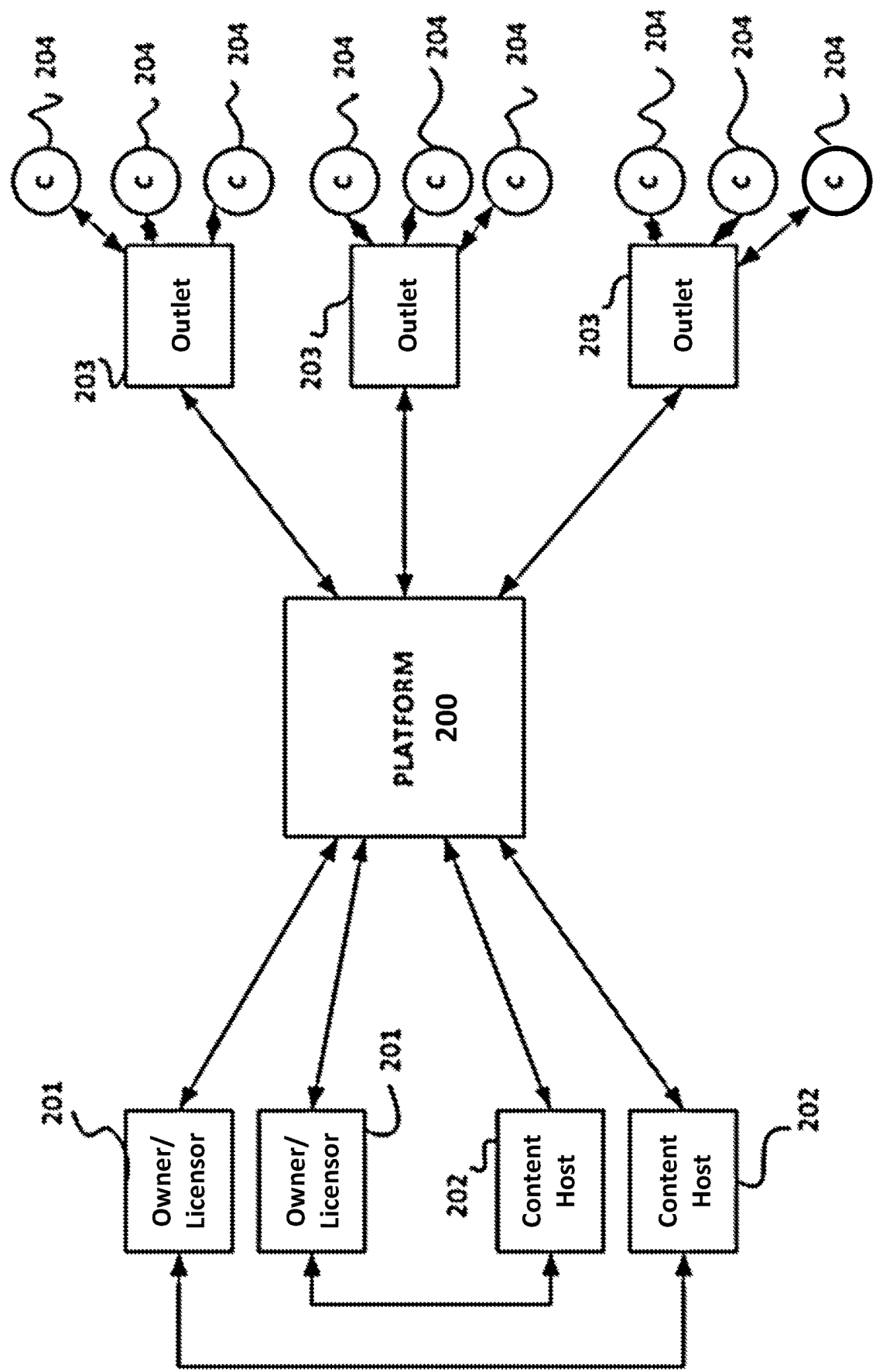
FIG. 2 is a dataflow diagram of a computing environment for syndicating the distribution of digital media through a network of outlets.

Referring to FIG. 2, exemplary communications between the various components of FIG. 1 will now be described in accordance with one or more embodiments. The platform 200 (e.g., software platform running on an ASP server 101) manages communications between the owners and/or licensors 201 (e.g., via content management servers 102) of the digital assets and their respective content hosts 202 (e.g., via content host servers 103), on the one hand, and a network of outlets 203 (e.g., outlet servers 104). The outlets 203 communicate with a plurality of end-users 204 (e.g., via remote devices 104 over a communications network), such as consumer(s), subscribers(s) or end-user(s).

As illustrated, the respective owners and/or licensors 201 may communicate with their content hosts 202 through the platform 200. It will be appreciated that the owners and/or licensors 201 may also communicate with the content hosts 202 directly, through a network or through other communications pathways for purposes not directly connected with this disclosure, e.g., communications related to, for example, promotional materials developed by outside developers who may also be the content hosts 202. Two-way communications may also take place between the owner(s) and/or licensor(s) 201 and the platform 200, and/or between the content hosts 202 and the platform 200. Two-way communications are also available between the platform 200 and the outlets 203, and the platform 200 may communicate to consumers via the outlets 203.

It will be seen from FIG. 2 that distribution of media assets originating at the owners and/or licensors 201, and/or the content hosts 202, may be distributed to consumers, subscribers or other end-users 204 via a syndication network of outlet(s) 203, who in turn offer the end-user, consumer or distributer interfaces thorough which to access and consume the digital assets, such as mobile applications and websites.

Figure 3A:
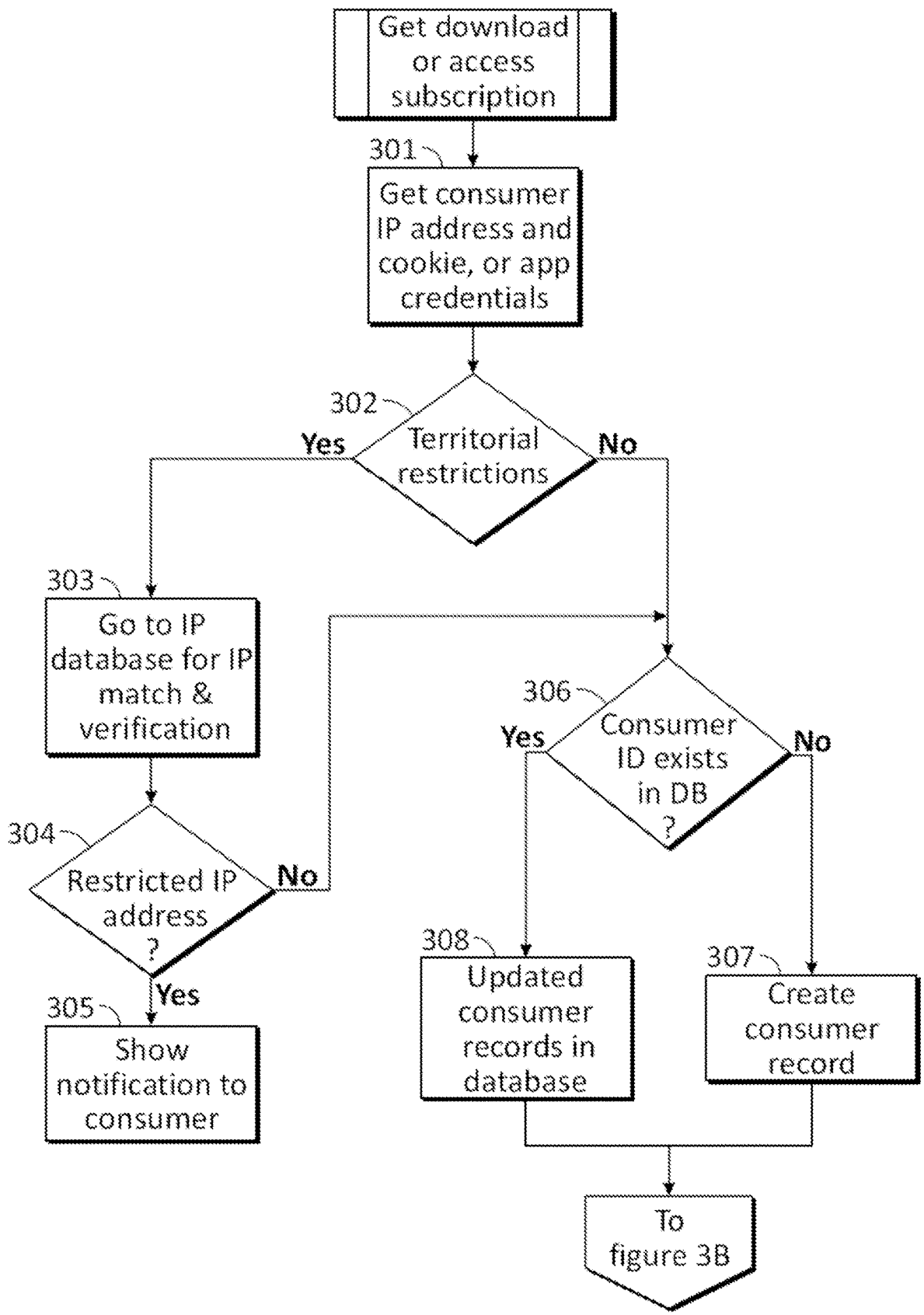
FIGS. 3A, FIG. 3B, FIG. 3C and FIG. 3D are a flow diagram illustrating a method for getting a download of a digital asset for a customer via an outlet in a syndicated distribution system of the present disclosure.

An embodiment of a process for delivering digital assets to end-users (including consumers and subscribers), will now be explained with reference to FIGS. 3A-D. Referring first to FIG. 3A, a process of delivering one or more digital assets to an end-user 204 begins when the end-user requests one or more digital assets through a media outlet 203 (see FIG. 2). In various embodiments, the end-user may request a download of a digital asset (e.g., a music file), access to a subscription, access to a digital media stream, creation of personalize digital content, or initiate another digital asset request.

The platform 200 first acquires identifying information for the end-user and/or end-user device. In the illustrated embodiment, the platform 200 acquires the Internet Protocol Address (IP address) of the end-user device, information stored in one or more cookies, and/or subscriber credentials for the application in Block 301. In the case of a mobile application ("app"), the platform may acquire a mobile app ID and subscriber credentials. In Block 302, a determination is then made as to whether there is a territorial restriction on each requested digital media asset. For example, the content owner may desire that a particular media asset be distributed in the United States but not in any of the countries of Europe or Asia. Information regarding territorial restrictions may be provided to the platform 200 by the media owner or operator and stored in a database associated with the media asset prior to distribution. If there is such a territorial restriction on the requested media assets, control passes to Block 303 where the platform 200 examines an IP database and/or country code from the end user payment form, to match and verify the address of the consumer with previous information connected with the consumer having that IP address, for example, third-party GeoIP data, that helps determine the end user's location.

In Block 304, a determination is made as to whether the IP address of the requesting consumer is a "restricted" one, that is, it is assigned to a geographical location other than the geographical location(s) in which the media owner(s) wishes distribution of the media asset(s) to take place in. If the IP address is "restricted," the process goes to Block 305, where a notification is sent to the consumer that the media asset(s) requested is unavailable in the consumer(s)'s geographical location of the consumer.

Returning to Block 302, if no territorial restriction had been placed on the requested media asset(s) by the media owner(s), the platform proceeds to Block 306. Similarly, if the IP address of the consumer was not a "restricted" one (as determined in Block 304), the platform also proceeds to Block 306. In Block 306, a determination is made as to whether record(s) of the consumer requesting the media asset(s) exists in the IP database. If it does, any necessary update(s) relating to the current transaction are made to the stored record(s) of the consumer, and the program proceeds to Block 309 of FIG. 3B. If, on the other hand, no record(s) of the particular consumer presently exist in the platform, a record of the consumer is made, and its cookie stored. The program then proceeds to Block 309 of FIG. 3B.

Figure 3B:
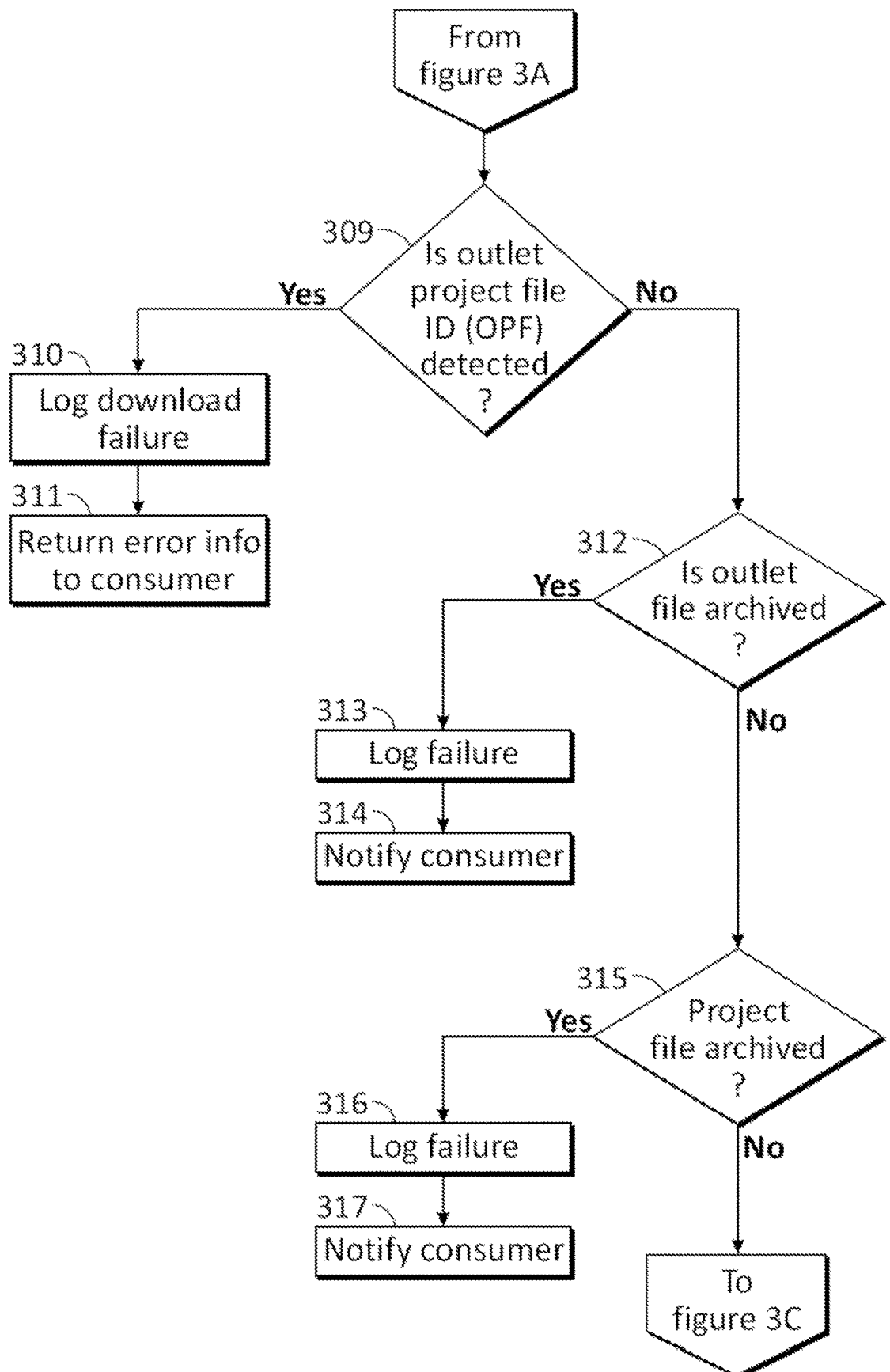

In Block 309 of FIG. 3B, a determination is made as to whether the project file(s) which contains the digital asset(s) requested by the consumer has been deleted. If the project file(s) which contains the digital asset requested by the consumer has been deleted, Block 311 is entered, where the occurrence of a download failure is logged into the system. In Block 311, error information is returned to the consumer, indicating the failure of the download.

Returning to Block 309, if the outlet project file has not been deleted, the program proceeds to Block 312, where a determination is made as to whether the outlet project file has been archived (i.e., is no longer available actively on the system). This outlet project file may contain information such as the user interface data (which is appropriate to the particular outlet servicing the consumer). If the outlet project file has been archived, failure of the download is logged in Block 313 and the consumer is notified of the failure of the download in Block 314.

If the outlet project file has not been archived in Block 312, Block 315 is entered, where a determination is made as to whether the appropriate outlet project file has been archived (i.e., is no longer available actively on the system). The outlet project file contains the media asset requested by the consumer. If the appropriate outlet project file has been archived (i.e., is no longer available actively on the system), a download failure is logged in Block 316 and the consumer is notified of the failure of the download in Block 317.

Figure 3C:
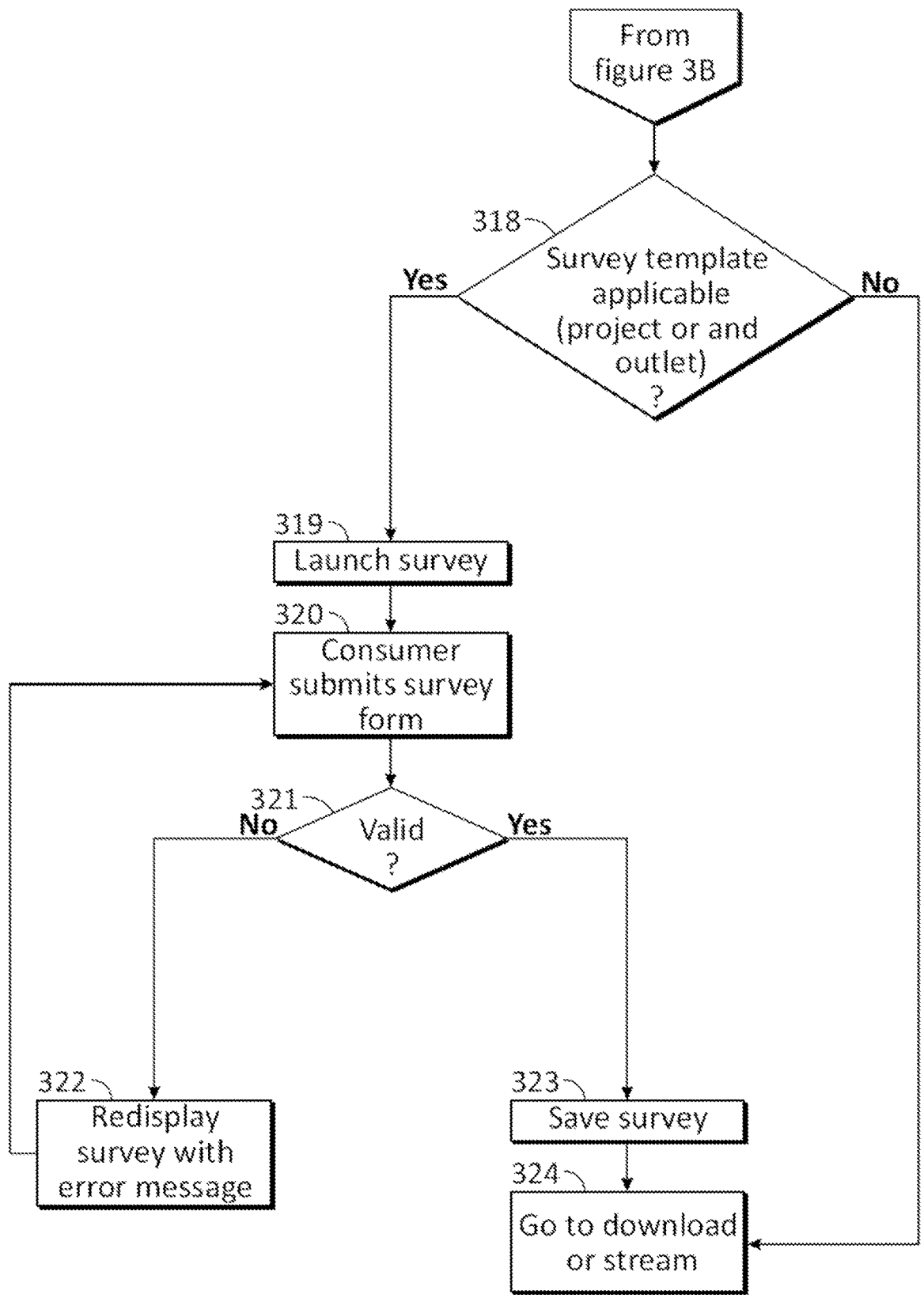
Figure 3D:
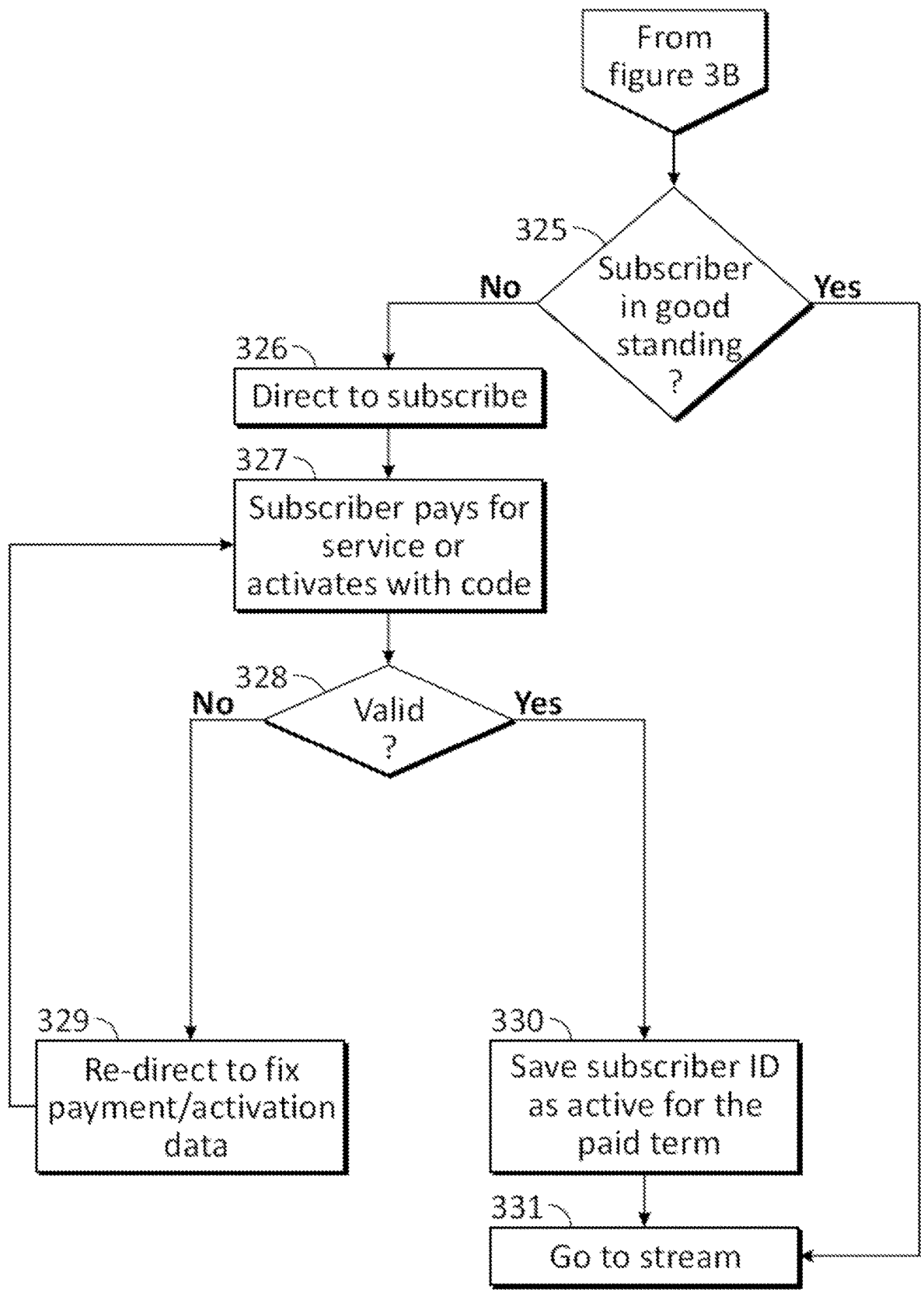

If the outlet project file has not been archived, the program proceeds to Block 318 of FIG. 3C, where a determination is made as to whether a survey template is applicable. Such a survey template may relate to a request for consumer information which is associated with either the particular project or the particular outlet servicing the consumer. If the survey template is applicable, the survey software is launched in Block 319, and the consumer submits a survey form with the required information in Block 320.

In Block 321, a determination is made as to whether the consumer completed the survey form correctly (i.e., is the form "valid"). If the survey form is not "valid," Block 322 is entered, where the survey form is re-displayed to the consumer with an error message requesting correction, and the program returns to Block 320, where the consumer re-submits the survey form. When the survey form is validly submitted (valid information provided by the consumer) the data collected by the survey is saved in Block 323, and the media asset requested by the consumer is downloaded to the consumer by the appropriate outlet using the user interface appropriate for that particular outlet.

Returning to Block 318, if there is no survey template associated with a particular project and/or outlet being utilized, Block 324 is entered directly, and the consumer gets the digital asset download or stream from the appropriate outlet using the user interface appropriate for that particular outlet. Conversely, in some services for other Outlets, instead of consumer arriving from Block 315 to Block 318, the consumer or subscriber arrive at FIG. 3D, Block 325, where a determination is made as to which subscription(s) the consumer has active on the Platform relevant to the outlet interface they are on. For example, a consumer operating an exercise apparatus may have a subscription for workout content (e.g., audio, video and other data associated with a workout class) through an outlet interface accessed through the exercise apparatus.

If the consumer has no active subscriptions, she may be notified to proceed to Block 326, which, via web site or app, she may subscribe to one or more channel(s). Activating channels in Block 327 can be done in multiple ways, depending on the outlet and the channel being accessed. For example, activation can be done via (i) monetary payment, (ii) gift card redemption, (iii) reward PIN code redemption, or (iv) crypto-currency or token purchase or redemption. Once the subscriber is authenticated in Block 328, the session is stored on the system in Block 330, and the subscriber proceeds to Block 331. If the validation process fails in Block 328, the subscriber is re-directed to fix her data and retry activation in Block 329. Returning to Block 325, if the subscriber's records show she is in good standing with an active streaming service or channel containing the desired track, then she proceeds directly to the track' stream or download, in Block 331.

FIG. 4A, FIG. 4B, FIG. 4C and FIG. 4D relate to a situation in which the media asset requested by the consumer will be supplied in an encrypted form and/or the owner(s), or licensor(s), of the media asset(s) desires certain restriction(s) to be placed on the consumer's use of the particular media asset(s), such as a limit in use to a time period selected by the owner/licensor. This may be useful, for example, in a situation where a record company is promoting an album and wishes to download one or more tracks from the album on a "complimentary" basis to promote the album but wishes the license to expire after a fixed period of time (e.g., thirty (30) days). Additional usage rules are available within various DRM software—for promotional purposes, as well as commercial usage and/or e-commerce purposes. For example, in some instances, a media asset is offered under a rental agreement (such as a movie rented for a 48-hours viewing window). In other cases, this process may be useful when the "License" is actually a cryptographic component that may or may not unlock the media asset, yet in any rate granularly tracks the rights components pre-encrypted in the file, allowing a crypto-currency system to track the media asset transaction for the benefit of its owners and stakeholders as may be tracked by a third party or by the said system itself.

Figure 4A:
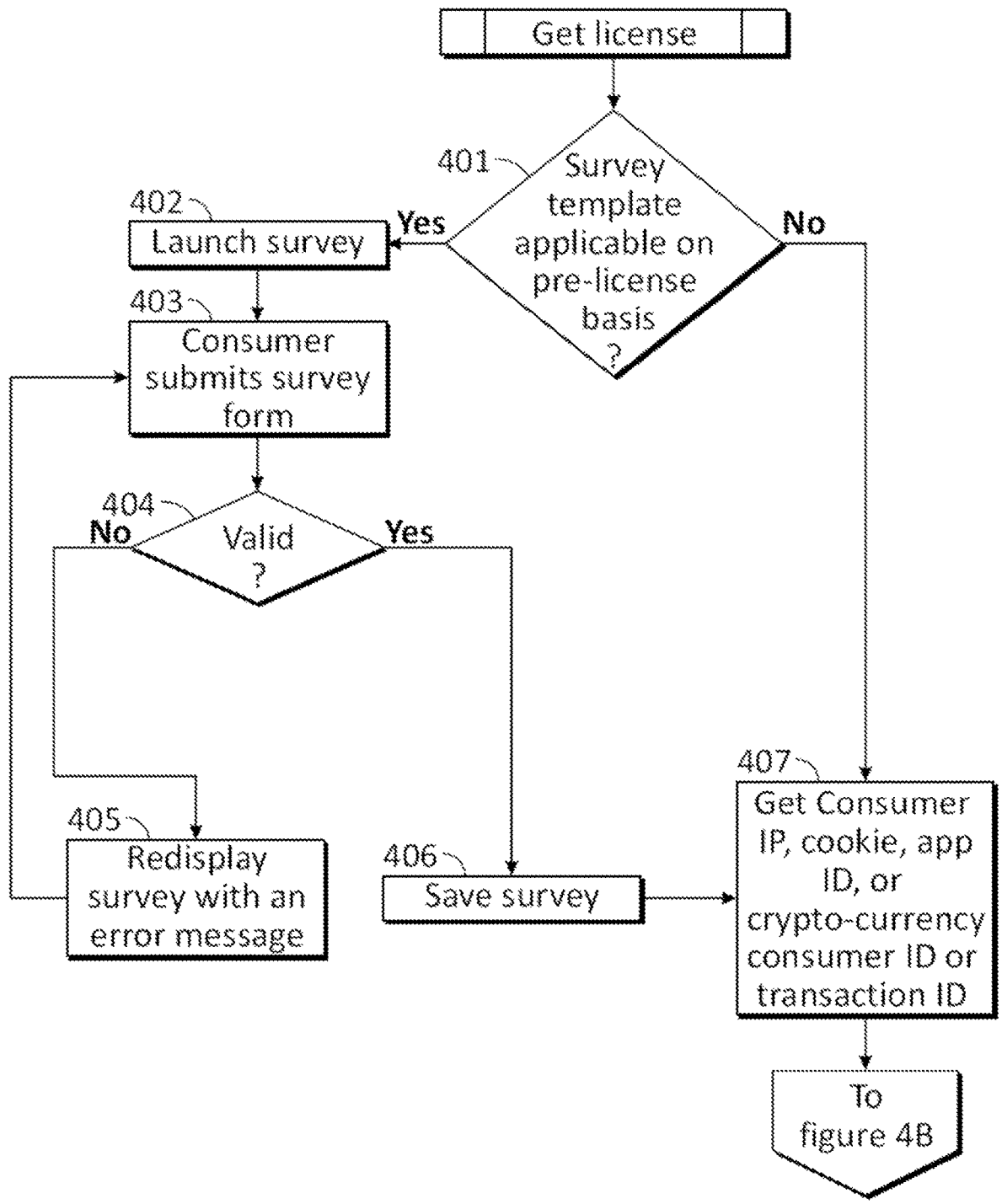
FIGS. 4A, FIG. 4B, FIG. 4C and FIG. 4D are a flow diagram illustrating a method for getting a license for the usage of a digital asset via an outlet in a syndicated distribution system.
Figure 4B:
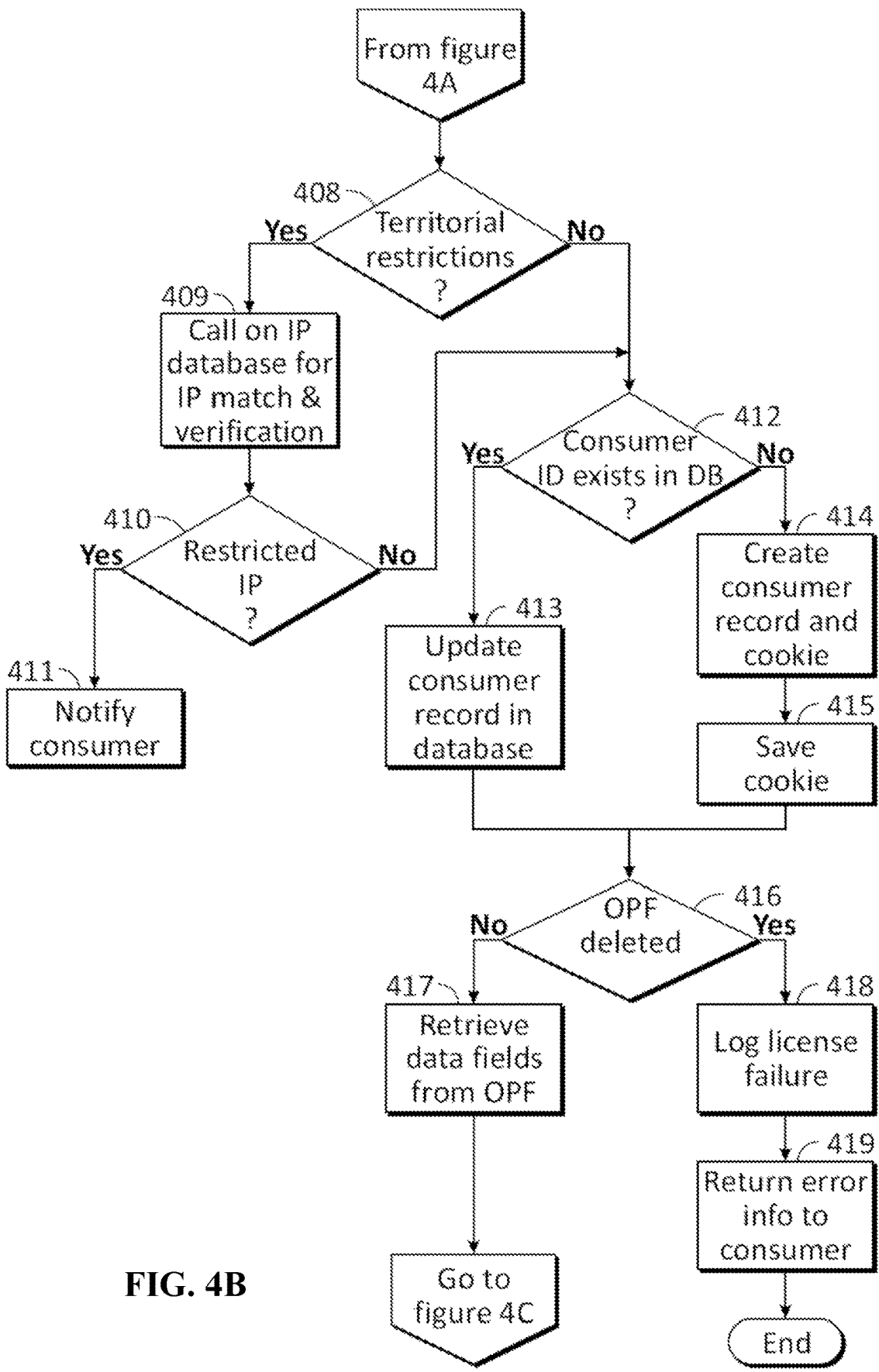
Figure 4C:
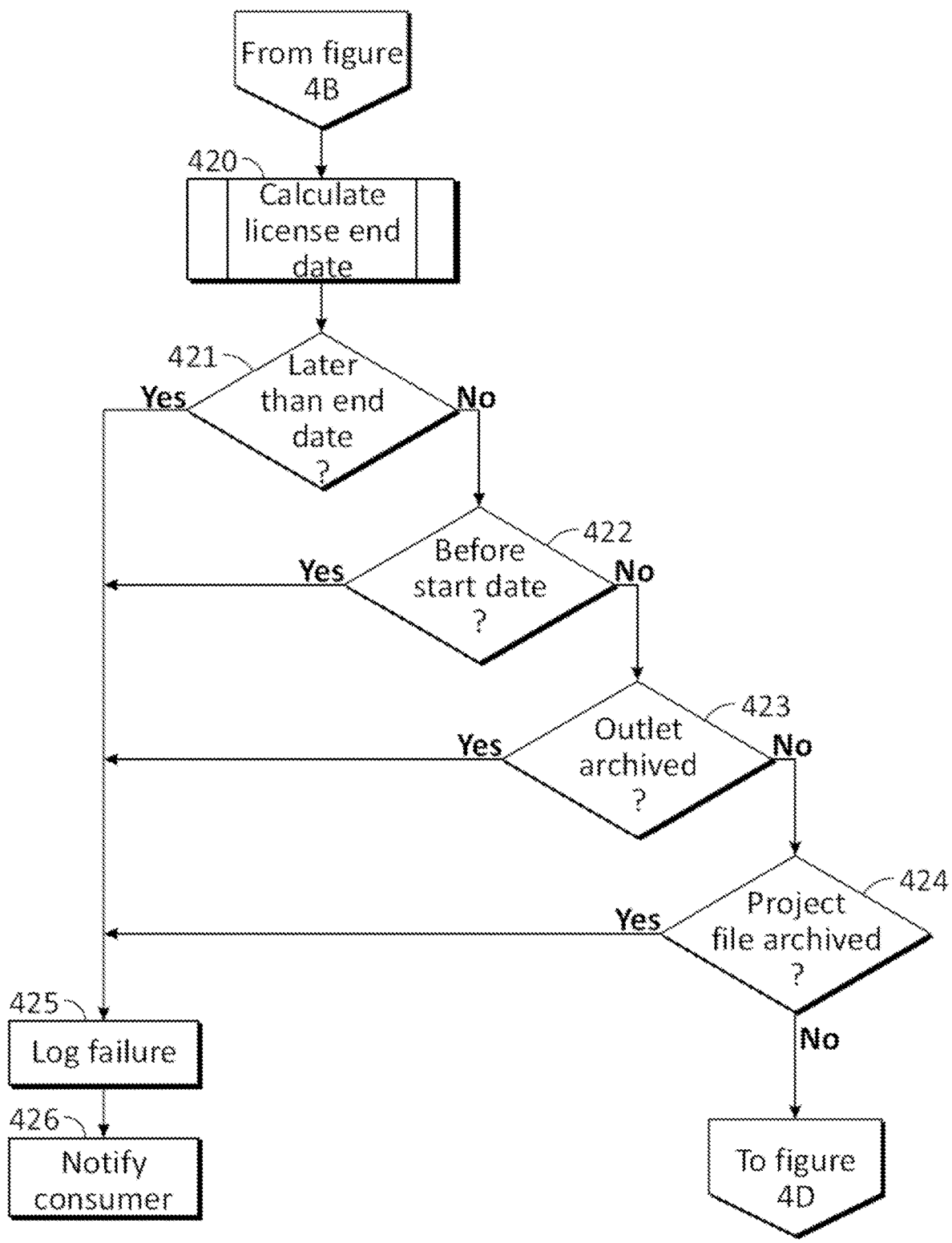

Referring to FIG. 4A, the licensing process begins at Block 401 of FIG. 4A, where a determination is made as to whether a survey template is applicable on a pre-license basis. That is, is the consumer required to complete a survey as a requirement for receiving the license. Such a survey may provide valuable demographic and/or marketing information to either the owner(s), or licensor(s), of the media asset(s), or to the outlet(s). Thus, the offering of a "free" license for a limited period of time may act as an incentive to the consumer to take the time to complete the requested survey. In other cases, the survey simply collects the end user's credentials as a crypto-currency user, enabling a transaction via file decryption by decentralized networks that thus track the activity into their ledger (such as Bitcoin, Ethereum, Litecoin, Ripple and other similar networks).

If a survey is applicable, Block 402 of FIG. 4A is entered and the survey software is launched. In Block 403, the consumer submits the survey form, and in Block 404, the information supplied by the consumer is examined for validity. If mistake(s) have been made by the consumer, Block 405 is entered, where the survey is re-displayed to the consumer with an error message, and the program returns to Block 403 where the consumer re-submits the survey form. If the survey information is "valid," the submitted information is saved in Block 406 and the platform gets the IP address of the consumer, the appropriate cookie, the appropriate app ID, and/or the appropriate crypto-currency consume ID or transaction ID in Block 407.

Returning to Block 401 of FIG. 4A, if the survey template is not applicable on a pre-license basis, Block 407 of FIG. 4A is entered directly. From Block 407 of FIG. 4A, the program proceeds to Block 408 of FIG. 4B, where a determination is made as to whether there is a territorial restriction on distribution of the requested media asset(s). If there is a territorial restriction on distribution of the requested media asset(s), Block 409 is entered, and the IP database is examined for an IP address match and verification with the IP address supplied by the requesting consumer. For the sake of clarification, in different reiterations of the system, the territorial restriction check can occur in different stages of the workflow.

In Block 410, a determination is made as to whether the IP address is restricted (i.e., the IP address is assigned to a territory other than the territory authorized for licensing by the owner(s), or licensor(s), of the media asset(s)). If the IP address is restricted, the consumer is so notified in Block 411. If the IP address is not restricted, or if there is no territorial restriction (as determined in Block 408 of FIG. 4B), the program proceeds to Block 412. In Block 412, a determination is made as to whether a record of the consumer exists in the platform. If such a record does exist, the record is updated with the saved data from the survey which the consumer may have just completed. If a consumer record does not exist, Block 414 is entered, and a record of the consumer is made, and then the appropriate cookie of the consumer is saved in Block 415.

In either case, the next step of the program is Block 416, where a determination is made as to whether the outlet project file record has been deleted. If the outlet project file record has been deleted, a license failure is logged in Block 418, and error information is returned to the consumer in Block 419, and the licensing sequence is then terminated. If the outlet project file record has not been deleted, the program goes to Block 417 of FIG. 4B, where data field(s) are retrieved from the outlet project file record. The program then proceeds to Block 420 of FIG. 4C, where a calculation is made as to the end date of the license, if any.

Next, in Block 421, a determination is made as to whether the present date is later than the end date of the license period desired by the owner(s), or licensor(s), of the media asset(s). For example, the license may be offered for a fixed period of time prior to, or concurrent with, the release date of the album which the licensed digital asset is associated with. If the end date has been "passed," a failure is logged in Block 425 and the consumer is so notified in Block 426. If the end date of the license has not already "passed," Block 422 is entered, where a determination is made as to whether the current date is prior to the start date of the license period determined by the owner, or licensor, of the digital media asset desired by the consumer.

If the present date is not prior to the start date of the license, Block 423 is entered, where a determination is made as to whether the outlet through which the consumer requested a license has been archived (i.e., is no longer active on the system). If the outlet project file has not been archived, Block 424 is entered, where a determination is made as to whether the outlet project file in which the desired media asset(s) exist has been archived (i.e., is no longer active on the system), and the program proceeds to Block 427 of FIG. 4D.

In the event that the current date is prior to the start date of the license of the digital media asset(s) requested by the consumer (as determined in Block 422), and/or the outlet through which the license has been requested has been archived (as determined in Block 423), and/or the outlet project file in which the digital media asset(s) exists has been archived (as determined in Block 424), the appropriate failure of the licensing process is logged in Block 425, and the consumer who had requested the license to utilize the digital media asset(s) is notified in Block 426.

Figure 4D:
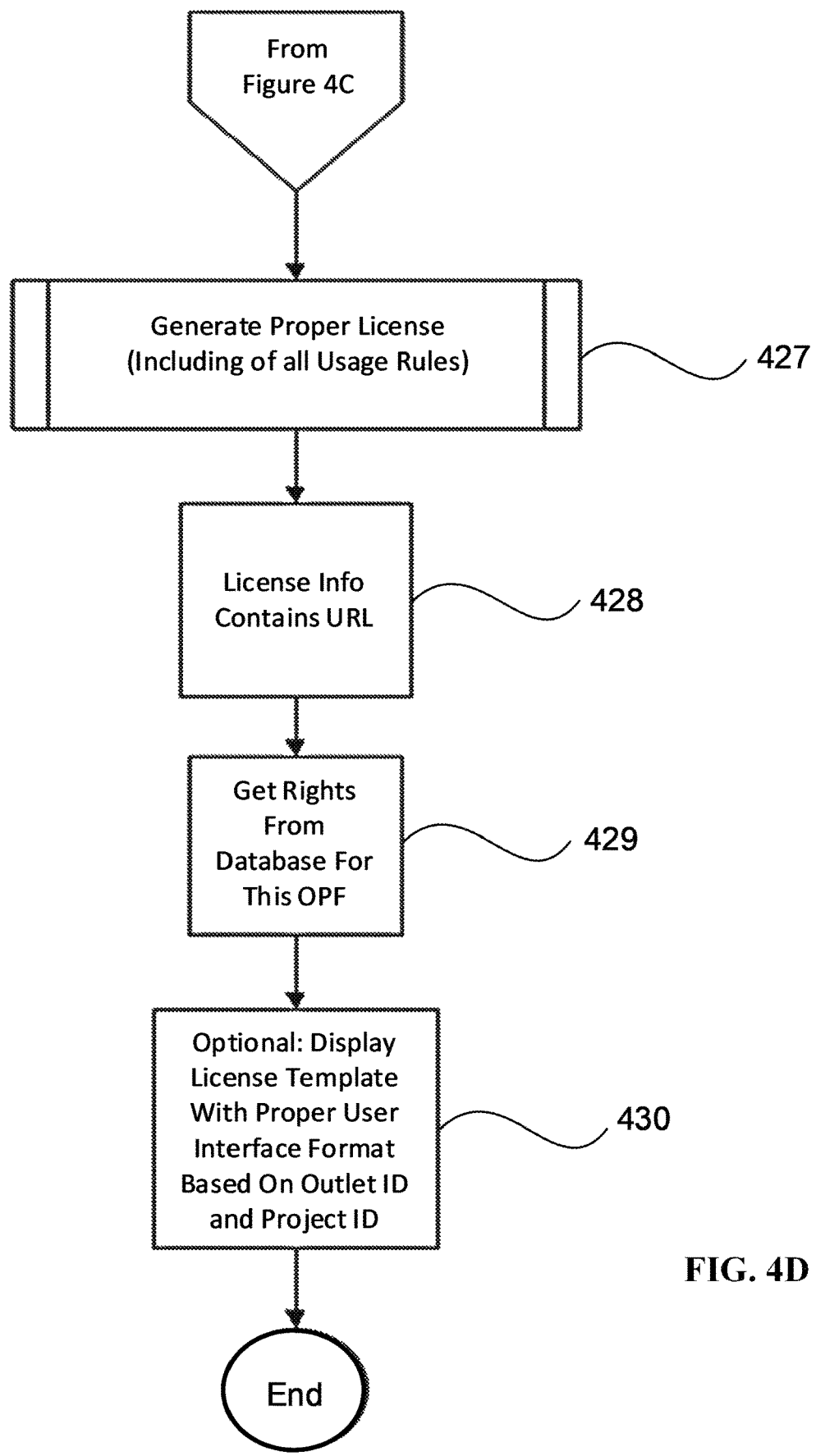

Referring to Block 427 of FIG. 4D, the proper license applicable to the consumer, outlet(s) and/or project(s) is generated. As indicated in Block 428, the license information contains the URL of the requested digital media asset(s). It may also be contained in the referenceable Smart Contract accompanying an applicable cryptography-based transaction. Next, in Block 429, the appropriate right(s) are retrieved from the service database and/or cryptography network for the particular outlet project file relating to the download or stream requested by the consumer. Finally, in Block 430, the license is delivered, and an option exists to display to the consumer a template with the appropriate user interface format based on the outlet identification and the project identification and full meta data.

Figure 5:
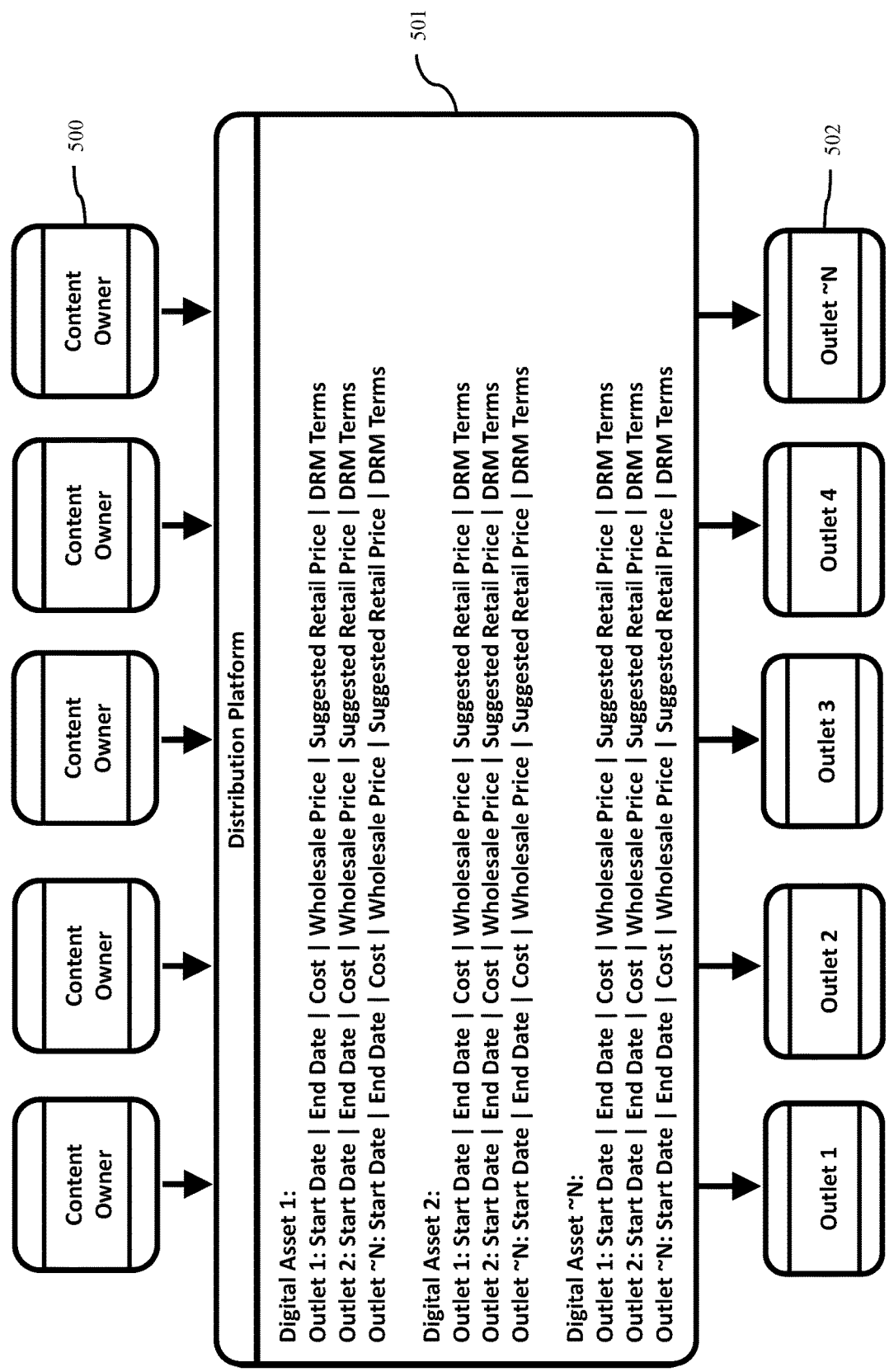
FIG. 5 is a dataflow diagram of a computing environment for the distribution of digital media in terms of the present disclosure.

Referring to FIG. 5, an example dataflow diagram is illustrated of a computing environment for the distribution of media assets by an envisioned B2B2C system. In the row of Blocks marked 500 we show the plurality of Content Owners who provide media assets into the Distribution Platform in Block 501.

The Content Owners may include various business attributes with their submissions, such as, on a per-media-asset basis (i) their territorial flags for countries in which the media asset may be exploited, (ii) for each such country or territory, their price for a sale of the product in local currency and numeric value, (iii) their allowance for the product to be included in subscriptions in that territory, and other content, pricing and distribution information. In some cases, the content owner may designate unique business attributes for only one or a few outlets in the Distribution Platform, while the rest of the outlets receive a different set of attributes. For example, a content owner may decide that a particular media asset should be sold exclusively at outlet 3 a week before it is available to all other outlets (a concept known as "windowing"), and perhaps also offer a cost discount for outlet 3 for the week. Other manageable parameters include, and are not limited to, DRM Terms, crypto-currency terms, suggested retail price (SRP), and start date and end date for various attributes. The administration of these granular changes is supported by the embodiment of the present invention, as exemplified by Block 501, supporting the proper data relationships to allow the decisions to be entered in the platform's administrative portal with ease.

Blocks 502 show how the media assets are exposed and provisioned for a plurality of merchant outlets. An outlet can exploit the media assets database created in Block 501 to create end-user offerings, from web sites selling downloads to mobile applications selling streaming subscriptions, and any other possibility enabled by business rules agreeable to the content owners. Outlets can view the usage rules provided to them per catalog owner and per product, and model their end-user offering accordingly, may it be a downloads model, streaming subscription model, or any other model. Outlets control their end-user experience, pricing, and catalog curation.

Figure 6:
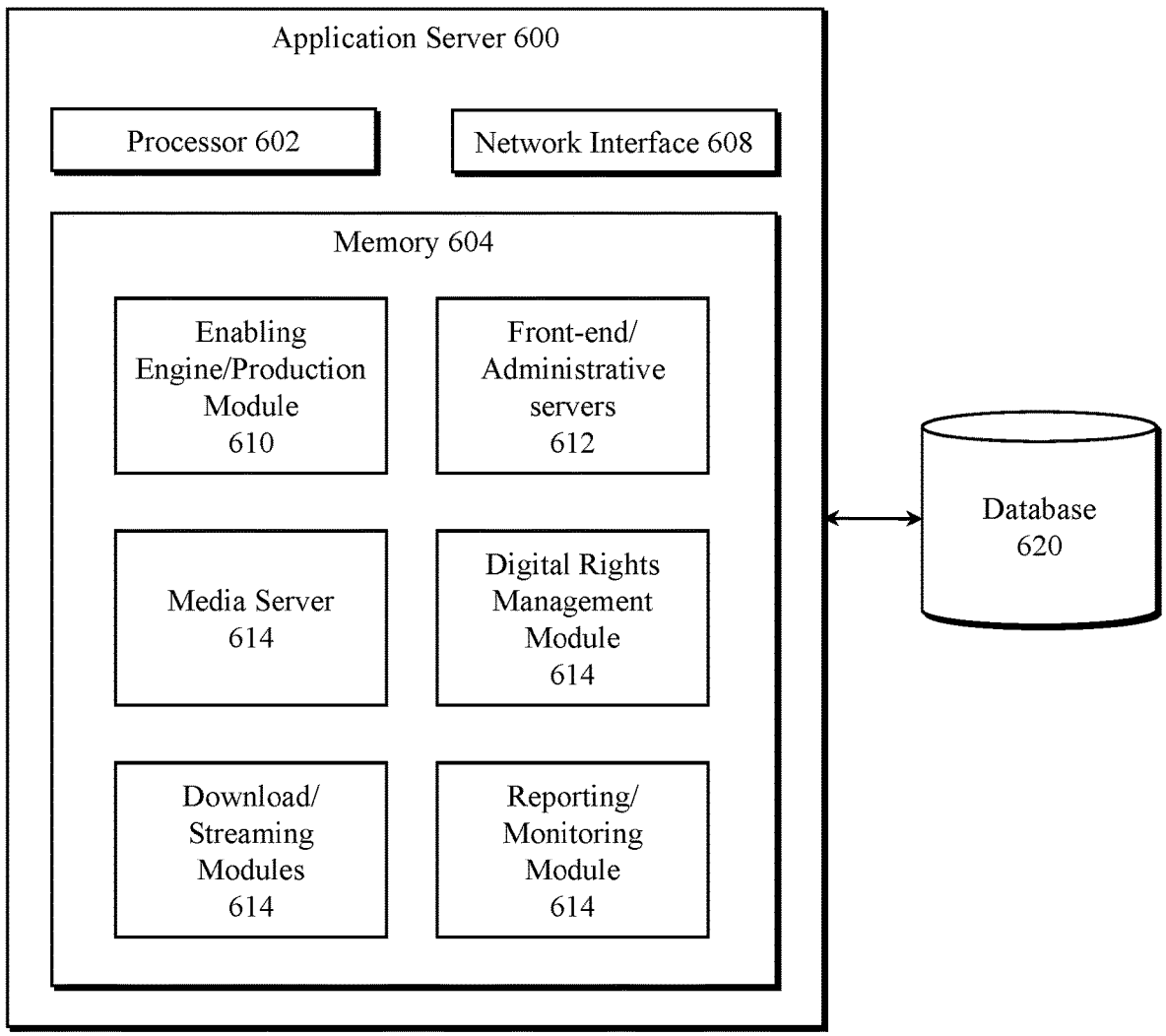
FIG. 6 is a block diagram of an application server for the distribution of digital media in accordance with an embodiment of the present disclosure.

The systems and methods disclosed herein can be embodied in a website that operates via the Internet or another network such as a wireless network. An exemplary application server 600 implement an embodiment of a distribution platform of the present disclosure is illustrated in FIG. 6. In one embodiment, the application server facilitates a website that executes on a processor-based platform, such as a Web server, that can be hosted by a system administrator or another administrative entity. The system may include one or more processors 602, memory components 604, and a database 620. The platform may include software instructions stored in the memory 604 for execution by the processor 602, including various logical components and processes as disclosed herein. In some the embodiments, the platform includes an enabling engine or production module 610, a front-end server and administrative servers 612, an encoder, a digital rights management module 614 (which may contain cryptography-based currency and token trading facilitation with a decentralized network), a media server 614 (e.g., a Windows Media server), a download manager module and a streaming manager module 614, and a reporting or monitoring module 614.

The platform can be configured with an enabling engine 610 to facilitate the production, hosting, and delivering of digital assets in accordance with the disclosure. The platform is further configured for the production, administration, and monitoring of one or more online promotions, sales initiatives, and subscription plans for one or more partners so that the partners can expose and deliver digital assets or content to one or more end-users or consumers. Finally, the platform is configured for the generation of detailed reports on all activities involving the production, hosting, delivering of digital assets including the production, administration, and monitoring of one or more online promotion, sale, or subscription plan involving the digital assets (e.g., through reporting/monitoring module 614). Each module of the platform is protected and ensures secure user access to each of the production, administration, and monitoring modules.

The database 620 and administration modules (e.g., implemented in administrative server 612) is configured to host digital assets such as media files, deliver digital assets, and manage licenses provided for the digital assets in a decoupled manner. For example, the database 620 or administration modules can provide a license and reporting only service, whereby a specific distributor can host particular digital assets on its own servers and deliver the files independently.

The enabling engine or production module 610 may include functionality to control and monitor the bandwidth, download rate, streaming plays, and maximum volume caps for all, or a portion of, the digital assets that are managed by the disclosure. This functionality provides careful control of budgetary constraints that may be placed on an associated client and any related digital assets.

The methods of the present disclosure may include a pricing provision where the price to the merchant of a specific content owner's catalog, or a subset thereof, is charged as a percentage of total merchant revenue from a la carte sales or from subscription sales revenue. The method includes the delivery of the digital content structured as a B2B2C (business-to-business-to-consumer) eco-system between a content owner (B) and a merchant outlet (B) and a subscriber (C). The platform disclosed herein provides a single platform between the B2B2C, which allows, through a single access for each stakeholder, the ability to each have control over availability dates and pricing specifications to a plurality of merchants and/or subscription outlets or channels.

Figure 7:
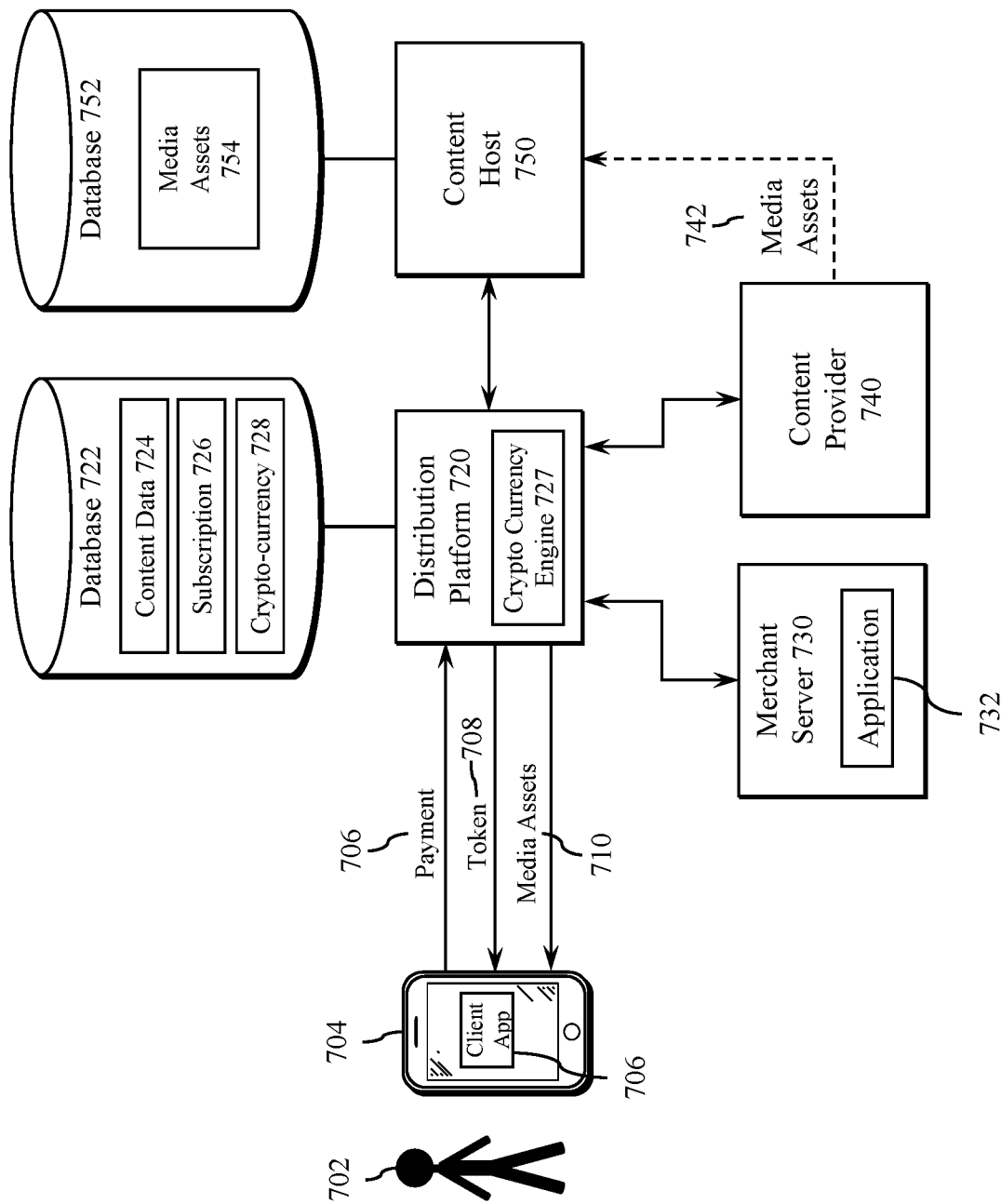
FIG. 7 is a dataflow diagram of a computing environment for the distribution of digital media using crypto-currency in accordance with an embodiment of the present disclosure.

An embodiment of an operation of a content distribution environment in accordance with one or more embodiments of the present application will now be described with reference to FIG. 7. The content distribution environment includes a distribution platform 720, which may be implemented as a network server as previously disclosed. The distribution platform 720 facilitates the delivery of digital content (such as media assets 742) to a user 702. The user 702 operates an end-user device 704, such as a mobile phone that includes a client application 706 facilitating communication with a merchant application 732 hosted on a merchant server 730 by a merchant. For example, in one embodiment the client application 706 may allow the user 702 to play music and the merchant application 732 may include a store allowing the user to access music files hosted through the distribution platform 720. In another example, the end-user device 704 may be associated with an exercise apparatus (e.g., a stationary bike, a treadmill) and the client application 706 provides an interface for accessing exercise related content through the merchant server 730. The exercise related content may include fully produced content such as a pre-recorded audio and/or video content, and/or may incorporate audio and/or video components that are being customized in real time based on certain data provided by the end user and/or by the exercise apparatus.

In some embodiments, user-generated content may be added into the service and weaved together with content-owner provided content in any media access and/or select subscription plan. The delivery of digital content into the platform may be facilitated via a plurality of supply-chain platforms which are used to deliver content directly to end-users through the merchant outlet and/or application. User-generated content may be added by the client application 706, merchant application 732 and/or content host 750. The merchant server 730 may facilitate one (or more) client applications (e.g., client application 706), and the mobile applications may represent a singular or a plurality of merchant outlets.

In the illustrated embodiment, the content provider 740 offers access to media assets 742 through a content host 750. The content host 750 includes a database 752 for storing and accessing the media assets 754. The content provider 750 manages access to the media assets 754 through the distribution platform 720, which includes a database 722 storing content data 724 and subscription data 726. The subscription data 726 organizes media assets into a unique subscription model, whereby multiple subscription plans can be produced, syndicated and administered on the distribution platform 720. Each such subscription offer can comprise of one or more subscription periods (i.e. daily, weekly, monthly, yearly, 5-year term, etc.), with each such period carrying its own subscription price, and wherein merchant outlets (e.g., through merchant server 730) are in essence subscription channels. The subscription price may be stated in currency or in any type of reward codes (i.e. stored value, promotional, pre-payment). A stand-alone "discount club" membership may be offered, covering some or all micro-channels in the service, and featuring steady percentile discount (which a certain cup) on select channels; and whereby said discount club could be sold via credit card or crypto currency.

In various embodiments, multiple micro-subscriptions may be offered by a specific merchant outlet via a unified OTT/mobile app or web page, with each such micro-subscription channel enabling its own branding, pricing, and content curation. One or multiple micro-subscriptions may be offered by the distribution platform via API services to be imbedded into one or more merchant outlets' own OTT/mobile app or web page.

The illustrated environment may also facilitate a crypto-currency value exchange. In one embodiment, the crypto-currency can be used to trade value associated with the subscription price, enabling subscription via crypto-currency purchase and/or facilitating subscription models where a crypto-currency token (e.g., token 708) is provided to the user 702 along with a subscription. The crypto-currency supporting each micro-channel subscription offering may include a unique crypto-currency and tokens (or coins). Selling off specific tokens can coincide with selling off a subscription period balance in a specific micro-subscription, in a system where trading in the value exchange of such coins is honored by the distribution platform 720, which may include a crypto-currency engine 727 and crypto-currency data 728 stored in the database 722.

The value of the micro-subscription offering may be gated by various content-related parameters such as, to name a few, the amount of digital data, selective song plays per period, or the total length of time listened to per period (e.g., so-called "metering). Channels may also accept content from end users. The content uploaded to the said micro-subscription channel may be uploaded in whole or in part by end users/subscribers, e.g., so-called user-generated content.

The micro-subscription offers one or more subscriber experiences, such as on-demand streaming, on-demand download, allowance downloads, tethered downloads, non-interactive streaming, or any highbred thereof. The subscription channel value for a period can be held in specific crypto-currency coins which end-users may trade with each other, directly or via crypto currency trading sites and platforms, thus trading in the balance of periods of subscription to a specific micro-channel in present value irrespective of past value paid at purchase.

In some embodiments, the subscription may be supported by tradable crypto-currency which provides benefits of a "fan club." Fans of an artist, for example, can fund the artist long term on a subscription or prep-paid subscription basis and receive a benefit in the form of crypto-currency. And fans of a fitness instructor, as another example, can fund their instructor long term on a subscription or pre-paid subscription basis and similarly receive a benefit in the form of crypto-currency. For example, owning a certain crypto-currency class can provide a limited discount period across all, or a certain finite volume of, micro-subscription channels. The value of such a club can easily be recognized by a subscriber who intends to subscribe to enough micro-subscriptions during a period so as to quickly recoup and benefit from the price of the fan club crypto-currency class. With such crypto-currency class being tradable as is the norm in crypto-currency offerings, the market may set higher valuation over time for the price of the fan club. Such secondary crypto-currency class within the envisioned platform can help sponsor platform enhancements, as well as help each channel stakeholder, such as said artist and said fitness instructor, raise necessary resources in order to further develop their content for their fans and invest in related content and infrastructure.

The platform may also provide for escrow services to monetary value provided through crypto-coin exchanges, where content owners in a channel receive the escrowed funds based on the delivery of milestones which they listed for the subscriber in their smart contract upon originally selling the crypto offering. For example, the content provider 740 may offer a pre-paid subscription for future content. The content provider 740 may be, for example, a musician who offers the pre-paid subscription to fund the creation of music content, or a personal trainer offering exercise related content to users of an exercise device. In some cases, content can be customized for the end user based on a historic performance data set available on merchant's servers, and/or based on the end user apparatus data provided in real-time during the end user's exercise.

The user 702 may use the client application 706 to access an application 732 on the merchant server 730 to purchase the pre-paid subscription. The user 702 may submit payment 706 (e.g., credit card payment, crypto-currency) through the distribution platform 720, which updates the subscription data 726 to associate the user 702 with the pre-paid subscription. The distribution platform 720 may further transmit tokens 708 to the end-user device 704, which may be used by the user 702 as previously discussed. After the content provider 740 creates the media assets 742 (e.g., an album of music), the media assets 742 may be provided to the content host 750. The media assets 742 are now available to users who meet certain access requirements, such as user who own a pre-paid subscription, through the distribution platform 720. The user 702 may use the client application 706 to download or otherwise access the media assets 710 from the distribution platform 720. In some cases, the end user streams the provided content. In other cases, the provided content may be customized in a dynamic and real time or close to real time rendering fashion based on data inputs from an end user exercise apparatus, related in whole or in part to end user's exercise performance.

Example: Content Distribution for Exercise Apparatus

Referring to FIGS. 8-12, an example embodiment facilitating the distribution of exercise related content will now be described. Embodiments of the present disclosure allow for efficient management of digital content, including the creation of multiple channels of distribution and payment models. The systems and methods disclosed herein provide numerous advantages to media consumers, content creators and merchants across a wide variety of applications.

In various embodiments, a merchant may access a distribution platform to facilitate the delivery and monetization of digital content. The merchant may curate one or more channels of digital content targeted for different end-user scenarios and set pricing and distribution restrictions for the channel. For example, a merchant may sell an exercise apparatus that includes a display and audio speakers for playing video and audio content. The merchant may offer digital content targeted to users of the merchant's exercise equipment, such as digital content associated with an exercise class led by a trainer. Using a local application associated with the exercise apparatus, the user may access digital content from the distribution platform. The local application may be associated with the merchant and/or the user, allowing the distribution platform to offer digital content associated with the exercise apparatus and/or the user. In this manner, the user may be provided with targeted digital content options and the merchant can control distribution of digital content to its exercise apparatus users to ensure a quality user experience.

The distribution platform also benefits content creators by facilitating content distribution and monetization. For example, an exercise instructor may offer additional content through his own channel and charge the user for the access on a per-use, subscription or another basis. Through the local application associated with the exercise apparatus, the user can engage exercise instructors though the distribution platform to secure individual coaching, personal training, class instruction and other exercise experiences. The instructor can establish one or more channels of instructor content and establish subscription and other payment models on the distribution platform. In some embodiments, the instructor and merchant establish an association through the distribution platform, allowing the instructor to distribute content through the merchant channel in a manner that may include revenue sharing model.

Figure 8A:
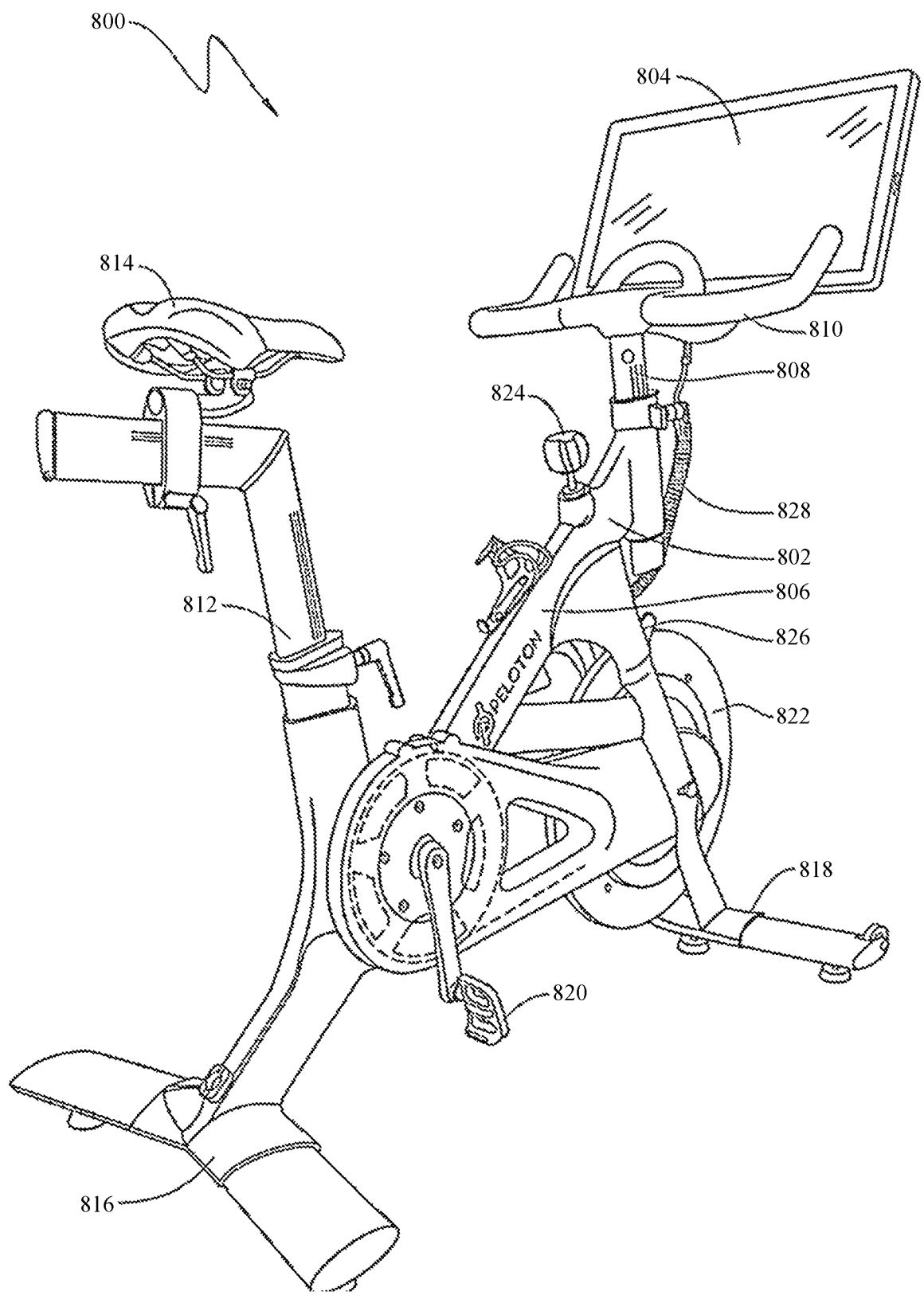
FIGS. 8A and 8B are rear perspective views of an exemplary a stationary bike, in accordance with an embodiment the present disclosure.
Figure 8B:
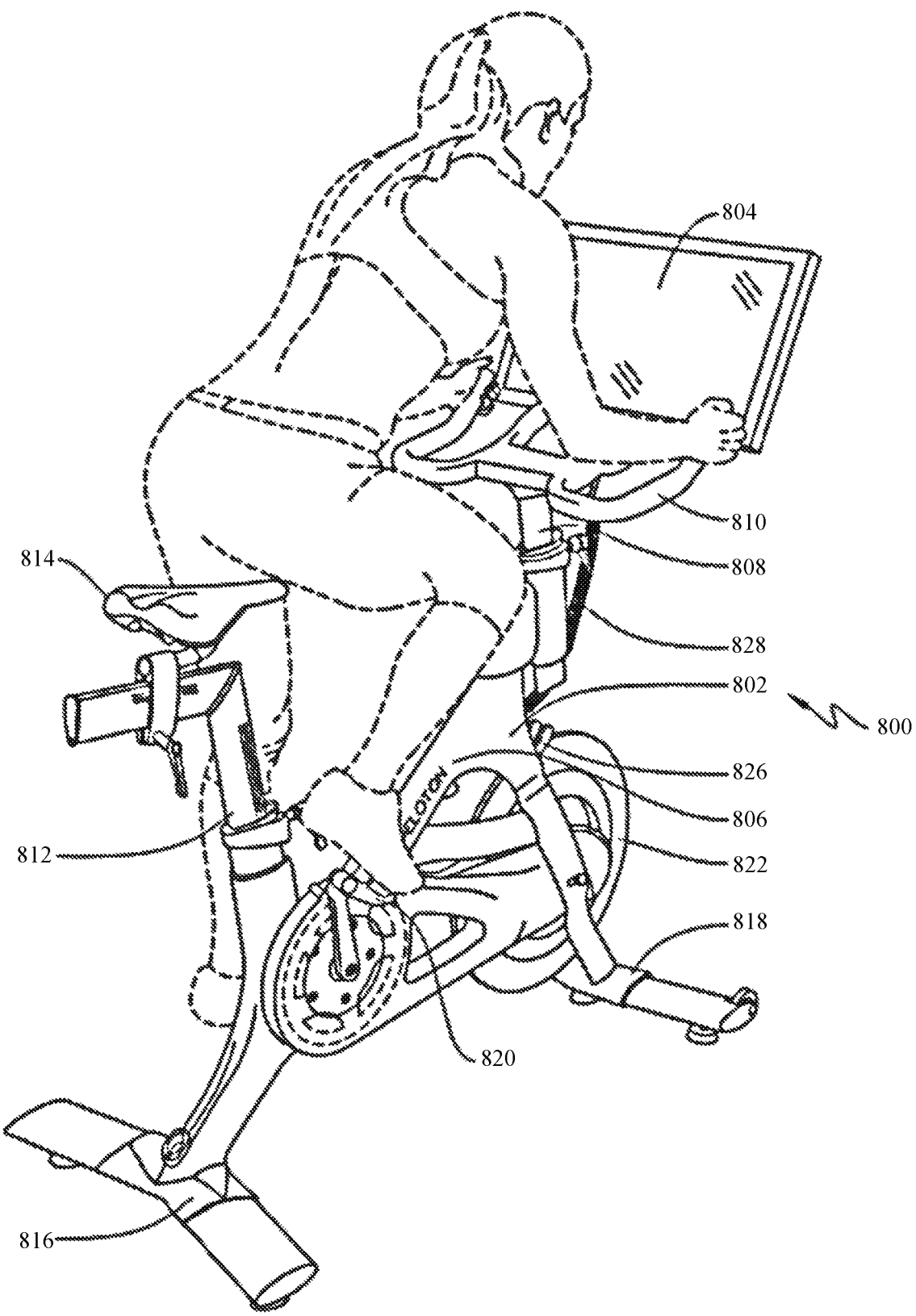

Referring generally to FIGS. 8A and 8B, various embodiments of an exercise apparatus will now be described. Although the embodiments illustrate an example with a stationary bike, exercise classes and other exercise related content, it will be appreciated that the present disclosure may be implemented with other exercise equipment and/or other content creation and delivery applications.

In various embodiments, local system 800 comprises a stationary bike 802 with integrated or connected digital hardware including at least one display screen 804. The stationary bike 802 may comprise a frame 806, a handlebar post 808 to support the handlebars 810, a seat post 812 to support the seat 814, a rear support 816 and a front support 818. Pedals 820 are used to drive a wheel 822 via a belt, chain, or other drive mechanism. The wheel 822 may be a heavy metal disc or other appropriate mechanism. In various exemplary embodiments, the force on the pedals necessary to spin the wheel 822 can be adjusted using a resistance adjustment knob 824. The resistance adjustment knob may directly or indirectly control a device that increases or decreases the resistance of the wheel to rotation. For example, rotating the resistance adjustment knob clockwise may cause a set of magnets 826 to move relative to the wheel, increasing its resistance to rotation and increasing the force that the user must apply to the pedals to make the wheel spin.

The stationary bike 802 may also include various features that allow for adjustment of the position of the seat 814, handlebars 810, etc. In various exemplary embodiments, a display screen 804 may be mounted in front of the user forward of the handlebars. Such display screen may include a hinge 828 or other mechanism to allow for adjustment of the position or orientation of the display screen relative to the rider.

The digital hardware associated with the stationary bike 802 may be connected to or integrated with the stationary bike 802, or it may be located remotely and wirelessly connected to the stationary bike. The display screen 804 may be attached to the stationary bike or it may be mounted separately but should be positioned to be in the line of sight of a person using the stationary bike. The digital hardware may include digital storage, processing, and communications hardware, software, and/or one or more media input/output devices such as display screens, cameras, microphones, keyboards, touchscreens, headsets, and/or audio speakers. In various exemplary embodiments these components may be integrated with the stationary bike. All communications between and among such components may be multichannel, multi-directional, and wireless or wired, using any appropriate protocol or technology. In various exemplary embodiments, the system may include associated mobile and web-based application programs that provide access to account, performance, and other relevant information to users from local or remote personal computers, laptops, mobile devices, or any other digital device.

In various exemplary embodiments, the stationary bike 802 may be equipped with various sensors that can measure a range of performance metrics from both the stationary bike and the rider, instantaneously and/or over time. For example, the stationary bike may include power measurement sensors such as magnetic resistance power measurement sensors or an eddy current power monitoring system that provides continuous power measurement during use. The stationary bike may also include a wide range of other sensors to measure speed, pedal cadence, wheel rotational speed, etc. The stationary bike may also include sensors to measure rider heart-rate, respiration, hydration, or any other physical characteristic. Such sensors may communicate with storage and processing systems on the bike, nearby, or at a remote location, using wired or wireless connections.

Hardware and software within the sensors or in a separate package may be provided to calculate and store a wide range of performance information. Relevant performance metrics that may be measured or calculated include distance, speed, resistance, power, total work, pedal cadence, heart rate, respiration, hydration, calorie burn, and/or any custom performance scores that may be developed. Where appropriate, such performance metrics can be calculated as current/instantaneous values, maximum, minimum, average, or total over time, or using any other statistical analysis. Trends can also be determined, stored, and displayed to the user, the instructor, and/or other users. A user interface may provide for the user to control the language, units, and other characteristics for the various information displayed.

In various exemplary embodiments the stationary bike 802 may be equipped with one or more large display screens 804, cameras, microphones, and speakers or other audio outputs. The display screen(s) 804 may be mounted directly to the stationary bike 802 or otherwise placed within the viewing area of the user. In various exemplary embodiments, at least one display screen is integrated into or attached to the stationary bike and is positioned in front of the rider generally centered on the handlebars 810 of the stationary bike as illustrated in the figures. Various mechanisms can be used to allow the user to customize the position of the display screen(s).

In an exemplary embodiment, a display screen 804 may be attached to the stationary bike 802 via a curved structure extending up and forward from the front stem of the frame 806. The curved structure may include a slot or aperture through it and extending along a portion of the length of the curved structure. A mounting post or similar structure on the display screen may attach to the curved structure, such as by a pin that passes through the mounting post or structure and the curved structure. In an exemplary embodiment, the pin may have a mechanism such as threads that allow it to be tightened to hold and lock the mounting post or structure at a particular location and position.

Display screen 804 may be driven by a user input device such as a touchscreen, mouse, or other device. In various exemplary embodiments a touchscreen display is mounted on the stationary bike generally centered between the handlebars and located just below the handlebars. The display screen may be any size, but optimally is large enough and oriented to allow the display of a range of information including one or more video streams, a range of performance metrics for the user and others, and a range of different controls.

In various exemplary embodiments the user can use a touchscreen or other interface to selectively present a range of different information on the screen including live and/or archived video, performance data, and other user and system information. The user interface can provide a wide range of control and informational windows that can be accessed and removed individually and/or as a group by a click, touch, or gesture. In various exemplary embodiments, such windows may provide information about the user's own performance and/or the performance of other participants in the same class both past and present.

The user interface can be used to access member information, login and logout of the system, access live content such as live exercise classes and archived content (referred to in the Figures as "Rides on Demand"). User information may be displayed in a variety of formats and may include historical and current performance and account information, social networking links and information, achievements, etc. The user interface can also be used to access the system to update profile or member information, manage account settings such as information sharing, and control device settings.

Figure 9A:
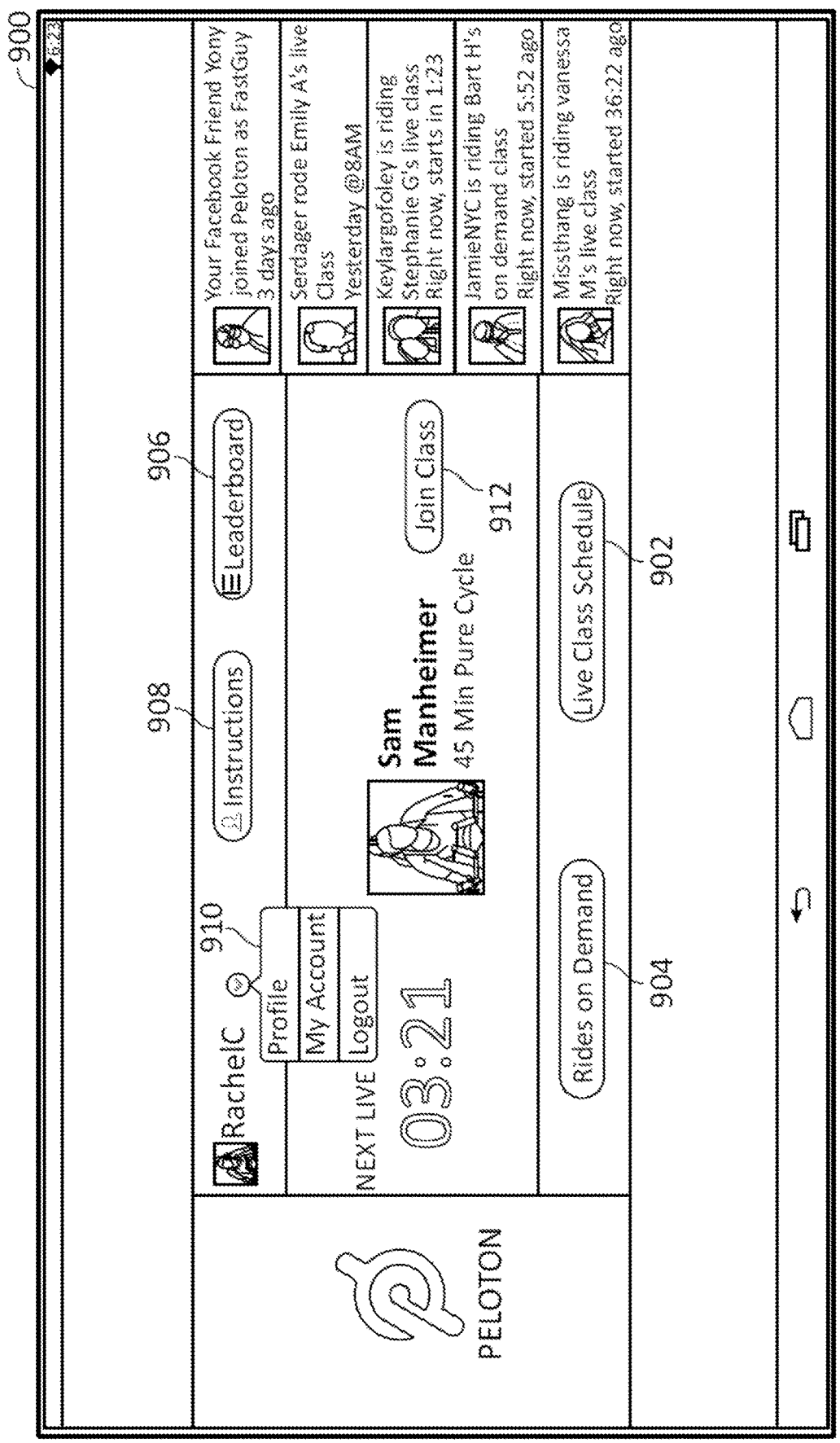
FIGS. 9A, 9B and 9C illustrated exemplary user interface screens for a stationary bike in accordance with an embodiment of the present disclosure.
Figure 9B:
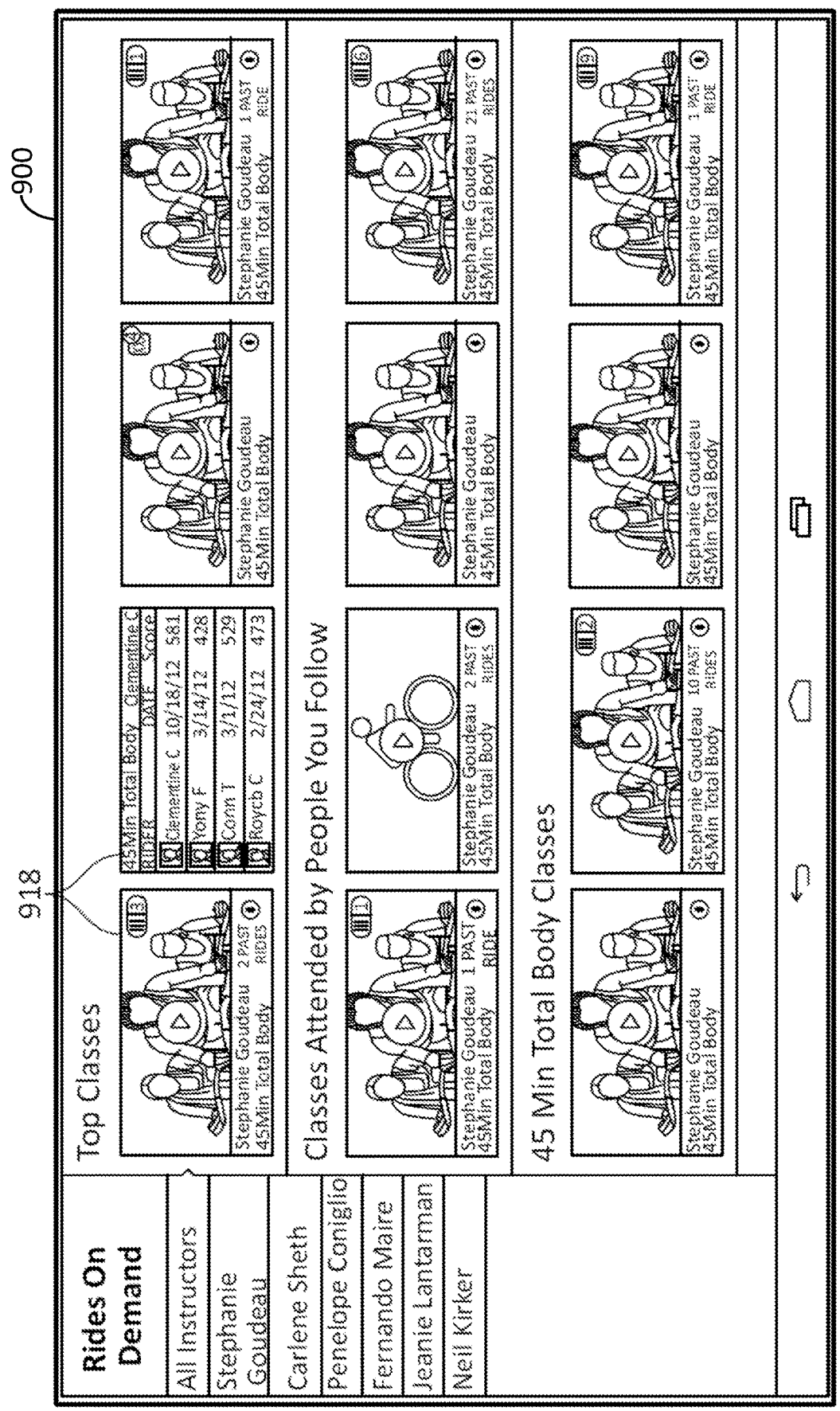
Figure 9C:
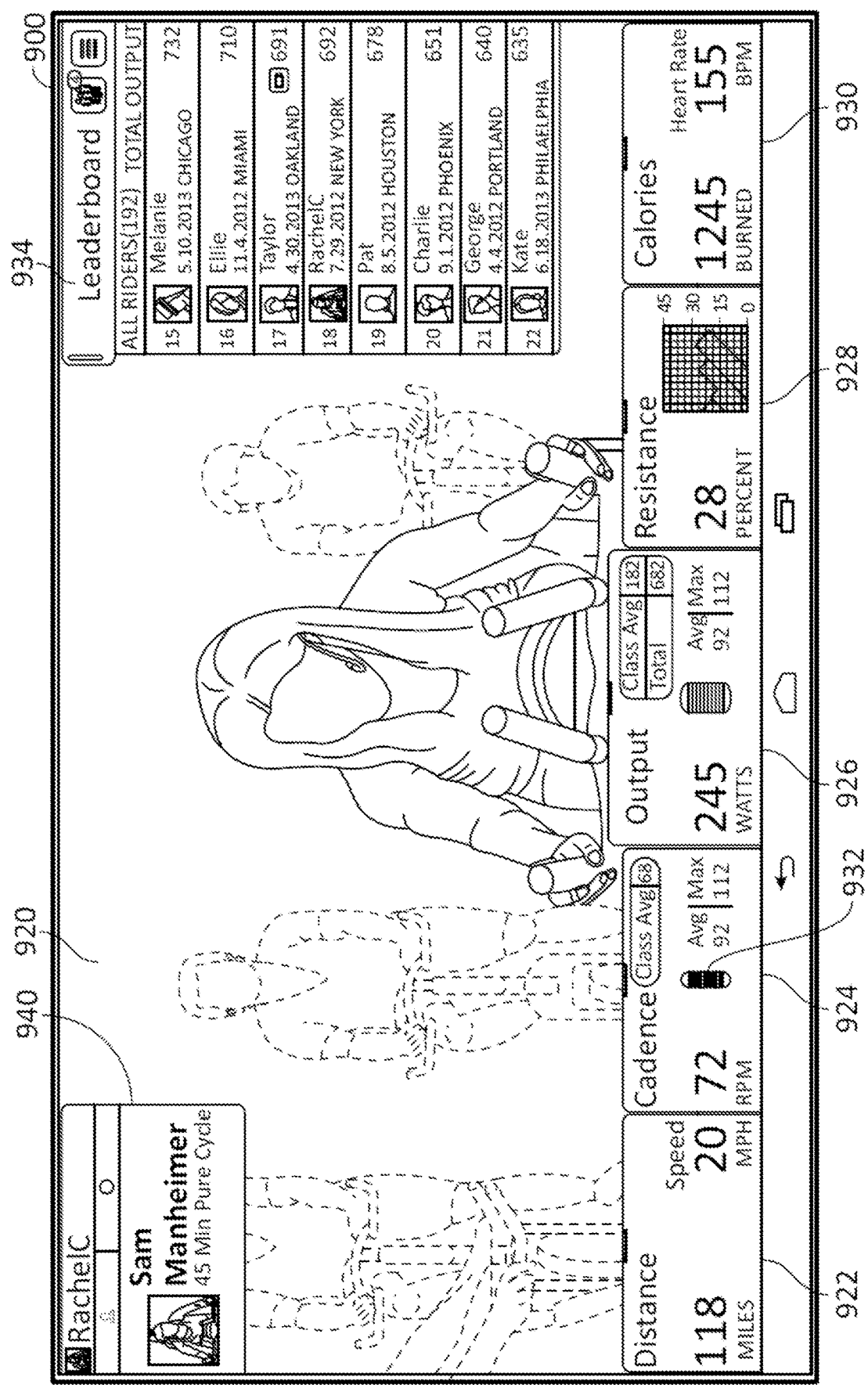

Referring to FIGS. 9A-9C, a user interface 900 may be presented on the display screen 904 to allow the user to manage their experience, including selecting information to be displayed and arranging how such information is displayed on their system. The user interface may present multiple types of information overlaid such that different types of information can be selected or deselected easily by the user. For example, performance information may be displayed over video content using translucent or partially transparent elements so the video behind the information elements can be seen together with the information itself.

The user interface 900 may present a variety of screens to the user, which the user can move among quickly using the provided user input device, including by touching if a touchscreen is used. In various exemplary embodiments, the user interface may provide a home screen that provides basic information about the system and available options. Referring to FIG. 9A, such a home screen may provide direct links to information such as scheduled classes 902, archived classes 904, a leaderboard 906, instructors 908, and/or profile and account information 910. The screen may also provide direct links to content such as a link to join a particular class 912. The user can navigate among the different screens in the user interface by selecting such links using the applicable input device such as by touching the touchscreen at the indicated location, or by swiping to bring on a new screen. The user interface may also provide other information relevant to the user such as social network information, and navigation buttons that allow the user to move quickly among the different screens in the user interface.

In various exemplary embodiments, the user can select among both live and archived content. For example, if the user selects scheduled classes 902, they may be presented with a screen showing the schedule of upcoming classes. The user interface allows users to select classes by time, instructor or rides type and/to start a class that is underway or about to begin. The class schedule may be presented in any suitable format, including calendar, list, or any other appropriate layout.

In various exemplary embodiments, if the user selects archived classes 904, they may be presented with a screen showing available archived classes sorted by any appropriate category. FIG. 9B shows an exemplary display of archived classes. Thumbnails or icons 918 representing archived classes may be displayed in any suitable format and may include information on how many times the user has ridden that class in the past or other performance or class-related information. A class may be accessed by selecting a particular thumbnail or icon.

Referring to FIG. 9C, when a class is being playing on the display screen through the user interface 900, in various exemplary embodiments the primary video feed may be shown as the background video full-screen or in a sub-window on the screen. Information elements may be provided on different parts of the display screen to indicate any performance metrics, including time ridden, elapsed time, time left, distance, speed, resistance, power, total work, pedal cadence, heart rate, respiration, hydration, calorie burn, and/or any custom performance scores that may be developed. The displayed information may also include the trend or relationship between different performance metrics. For example, the display can indicate a particular metric in a color that indicates current performance compared to average performance for a class or over time, such as red to indicate that current performance is below average or green to indicate above average performance. Trends or relative performance can also be shown using color and graphics, such as a red down arrow to show that current performance is below average.

A primary window 920 showing the live or archived class that the user selected. In various exemplary embodiments, performance metric windows 922, 924, 926, 928, and 930 may show specific performance metrics for the user's current ride, past rides, or other performance information. Such performance metric windows may be presented anywhere on the display screen and may be user selectable such that they can be displayed or removed by a screen touch or gesture.

As shown in FIG. 9C, window 922 displays distance and speed. Window 924 displays current pedal cadence, along with the user's average and maximum cadence and the class average, and an indicator arrow 932 showing whether the user's cadence is increasing or decreasing. Window 926 shows power output in watts, together with average output, maximum output, class average, and total output, along with a similar indicator arrow. Window 928 shows resistance as both a number and graphically, and window 930 shows calories burned and heart rate.

The user interface may allow the user to toggle between display of maximum, average, and total results for different performance metrics. The user interface may also allow the user to hide or display information elements, including performance metrics, video streams, user information, etc. all at once or individually. Performance information can also be displayed in various display bars that can be hidden or displayed as a group or individually. The user interface may provide for complete controls for audio volume, inputs, and outputs as well as display output characteristics.

A leaderboard 934 may also be displayed to allow the user to see their performance in comparison to others taking the same class. In various exemplary embodiments, a leaderboard may be configured to display the relative performance of all riders, or one or more subgroups of riders. For example, the user may be able to select a leaderboard that shows the performance of riders in a particular age group, male riders, female riders, male riders in a particular age group, riders in a particular geographic area, etc. Users may be provided with the ability to deselect the leaderboard entirely and remove it from the screen. In various exemplary embodiments, the system may incorporate various social networking aspects such as allowing the user to follow other riders, or to create groups or circles of riders. User lists and information may be accessed, sorted, filtered, and used in a wide range of different ways. For example, other users can be sorted, grouped and/or classified based on any characteristic including personal information such as age, gender, weight, or based on performance such as current power output, speed, or a custom score.

The leaderboard 934 may be fully interactive, allowing the user to scroll up and down through the rider rankings, and to select a rider to access their detailed performance data, create a connection such as choosing to follow that rider, or establish direct communication such as through an audio and/or video connection. The leaderboard may also display the user's personal best performance in the same or a comparable class, to allow the user to compare their current performance to their previous personal best. The leaderboard may also highlight certain riders, such as those that the user follows, or provide other visual cues to indicate a connection or provide other information about a particular entry on the leaderboard. In various exemplary embodiments, the leaderboard will also allow the user to view their position and performance information at all times while scrolling through the leaderboard.

In various exemplary embodiments, the system calculates and displays one or more custom scores to describe one or more aspects of the users' performance. One example of such a custom score would be a decimal number calculated for a particular class or user session. Such a score could also be calculated using performance data from some or all classes or sessions over a particular period of time. In an exemplary embodiment, the custom score takes into account the amount of time ridden, total work during that time period, and number of classes in a given time period.

In various exemplary embodiments, performance information about other users may be presented on the leaderboard 934 or in any other format, including formats that can be sorted by relevant performance parameters. Users may elect whether or not to make their performance available to all users, select users, and/or instructors, or to maintain it as private so that no one else can view it.

In various exemplary embodiments the user interface may also present one or more video streams from a range of different sources. For example, one video stream may be the live or archived class content shown in the primary window, while one or more additional video streams may be displayed in other windows on the screen display 804. The various video streams may include live or recorded streaming instructor video or any other video content, including one or more live video chat streams.

The user interface may also provide additional windows that can be used to display a range of content including additional performance data, information about the class, instructor, other riders, etc., or secondary video streams. Such additional windows can allow the user to see a range of information regarding other current or past participants to compare performance, and open or close voice or video chat streams or other communication channels. In various exemplary embodiments the user can simultaneously access other content including movies, television channels, online channels, etc. A secondary window 940, 942, 944 may display a range of information and content. Secondary window 940 displays the name of the user, the name of the current class and basic class information.

Example: Content Creation and Distribution for Exercise Apparatus

Figure 10:
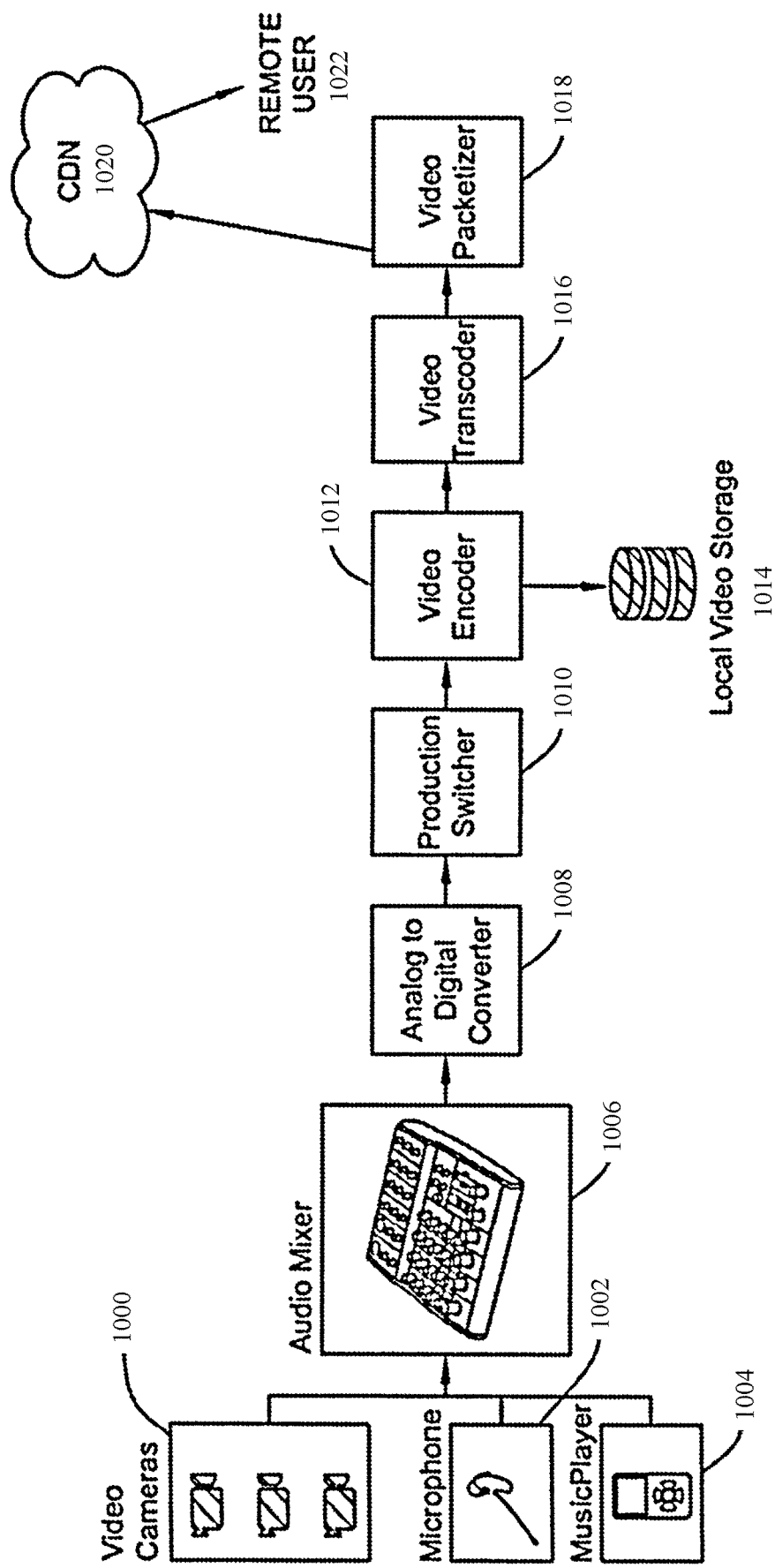
FIG. 10 shows an exemplary data flow for content creation and distribution for a stationary bike, in accordance with an embodiment of the present disclosure.

Referring to FIG. 10, an embodiment of a system for distributing content to an exercise apparatus will now be described. Content for an exercise class experience may be generated by a content provider (e.g., exercise instructor) using one or more video cameras 1000, an instructor microphone 1002, and a music player 1004 as inputs to an audio mixer 1006. The audio mixer outputs content to an analog to digital converter 1008, which provides converted data to a production switcher 1010. The production switcher sends the production video to a video encoder 1012, which stores the encoded video to a local storage device 1014 and sends it to a video transcoder 1016. The video transcoder outputs the transcoded data to a video packetizer 1018, which then sends the packetized data stream out through the content distribution network 1020 (such as described above with reference to FIGS. 1-7) to remote system users 1022. In various exemplary embodiments, instructors and/or users may be provided with access to a content creation platform that they can use to help them create content. Such a platform may provide tools for selecting and editing music, managing volume controls, pushing out chat or other communications to users, defining payment criteria, defining subscription criteria, and other content distribution criteria as discussed herein.

As described above, through the user interface on their stationary bike 802, users may access lists, calendars, and schedules of live and recorded cycling classes available for delivery through the display screen 804. In various exemplary embodiments, once the user selects a class, the local system accesses and displays a primary data stream for the class from the content distribution platform of the present disclosure. This primary data stream may include video, music, voice, text, or any other data, and may represent a live or previously recorded cycling class. The local system may be equipped for hardware video accelerated encoding/ decoding to manage high definition video quality at up to 1080 pixels based on existing technology. The local system may automatically adjust bitrate/quality of the data stream for the class in order to bring rider the highest quality video according to user's bandwidth/hardware limitations.

In various exemplary embodiments, the networked exercise systems and methods may include multi-directional communication and data transfer capabilities that allow video, audio, voice, and data sharing among all users and/or instructors, and the various components of the content distribution platform of the present disclosure (including a merchant application server and the content provider). This allows users to access and display multi-directional video and audio streams from the instructor and/or other users regardless of location, and to establish direct communications with other users to have private or conferenced video and/or audio communications during live or recorded classes. Such data streams can be established through the local system 800 for presentation via the display screen 804 the primary window or in a secondary window. In various exemplary embodiments, users can manage multiple data streams to select and control inputs and outputs. The local system may allow the user to control the volume of primary audio stream for the class as well as other audio channels for different users or even unrelated audio streams such as telephone calls or their own music selections. For example, this would allow a user to turn down the instructor volume to facilitate a conversation with other users. Such data streams may be mixed with media assets provided from one or more content providers through the content distribution platform.

For live classes, in various exemplary embodiments the instructor may have the ability to communicate with the entire class simultaneously or to contact individual users and solicit feedback from all users regardless of location in real-time. For example, instructors could ask users verbally, or text a pop-up message to users, seeking feedback on difficulty level, music choice, terrain, etc. Users could then respond through their onboard system by selecting an appropriate response or providing verbal feedback. This allows instructors to use crowdsourcing to tailor a class to the needs of the participants, and to improve their classes by soliciting feedback or voting on particular class features or elements.

In various exemplary embodiments, instructors may also be able to set performance targets, and the system can measure and display to the user and the instructor their performance relative to the target. For example, the instructor may set target metrics e.g. target power and cadence, then display this next to users' readings with a color coding to indicate whether or not the user is meeting this target. The system may allow the instructor to remotely adjust bike settings for individual users.

In various exemplary embodiments, users can control access to their own information, including sensor data, performance metrics, and personal information. Such data can be held at the local system, transmitted for storage and management by a remote system and shared with other users, or stored remotely but not shared with other users. Users may also elect to disclose their presence on the system to other users, or to participate in a class without making their presence known to other users. Such data can be securely shared with content generators to generate real time media content in response to the sensor data, performance metrics and other class related information.

In various exemplary embodiments, users can access a list of all or selected current and/or past class participants. Such lists may include performance information for such users, such as total power, speed, cadence, resistance, or a custom score that provides information about relative user performance. Such lists may also include controls to allow the user to open up live streams to the user such as live video chat streams.

System Features and User Resources

In various exemplary embodiments, the networked exercise system and methods may allow users to create accounts and save and manage their performance data. As discussed above, the system may allow users to browse schedules for upcoming live classes, signup for future live streaming classes, and setup reminders. Users may also be able to invite others to participate in a live class, and setup text, email, voice, or other notifications and calendar entries. Users may be able to access system, account, performance, and all other data via web-based or application-based interfaces for desktop and/or mobile devices, in addition to the user interface for the local system 800 associated with their stationary bike 802.

In various exemplary embodiments, the system can provide for simultaneous participation by multiple users in a recorded class, synchronized by the system and allowing access to all of the same communication and data sharing features that are available for a live class. With such a feature, the riders simultaneously participating in the same archived class can compete against each other, as well as against past performances or "ghost" riders for the same class.

Figure 11:
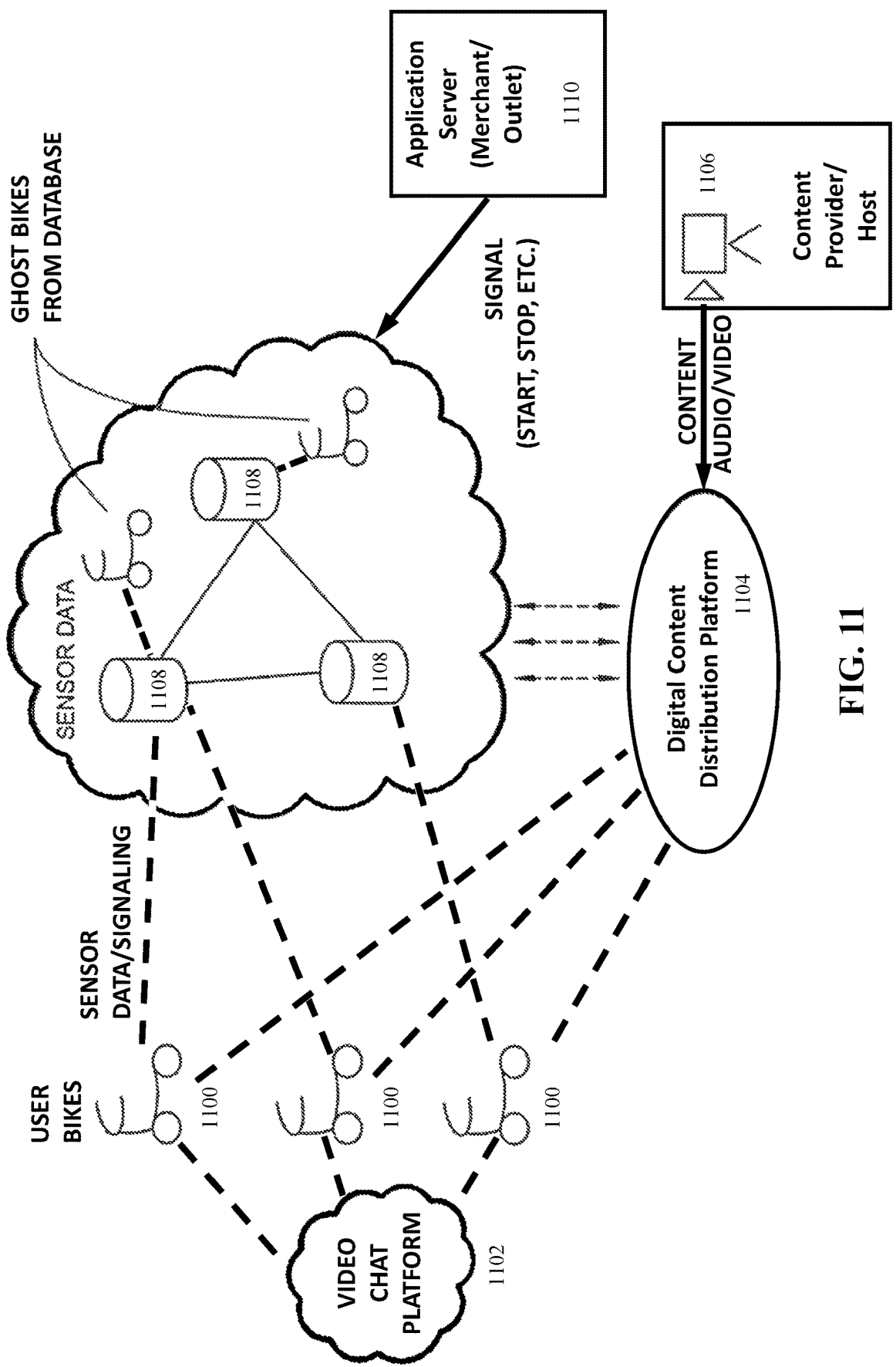
FIG. 11 is an illustration of an exemplary network architecture for use with a stationary bike, in accordance with an embodiment of the present disclosure.
Figure 12:
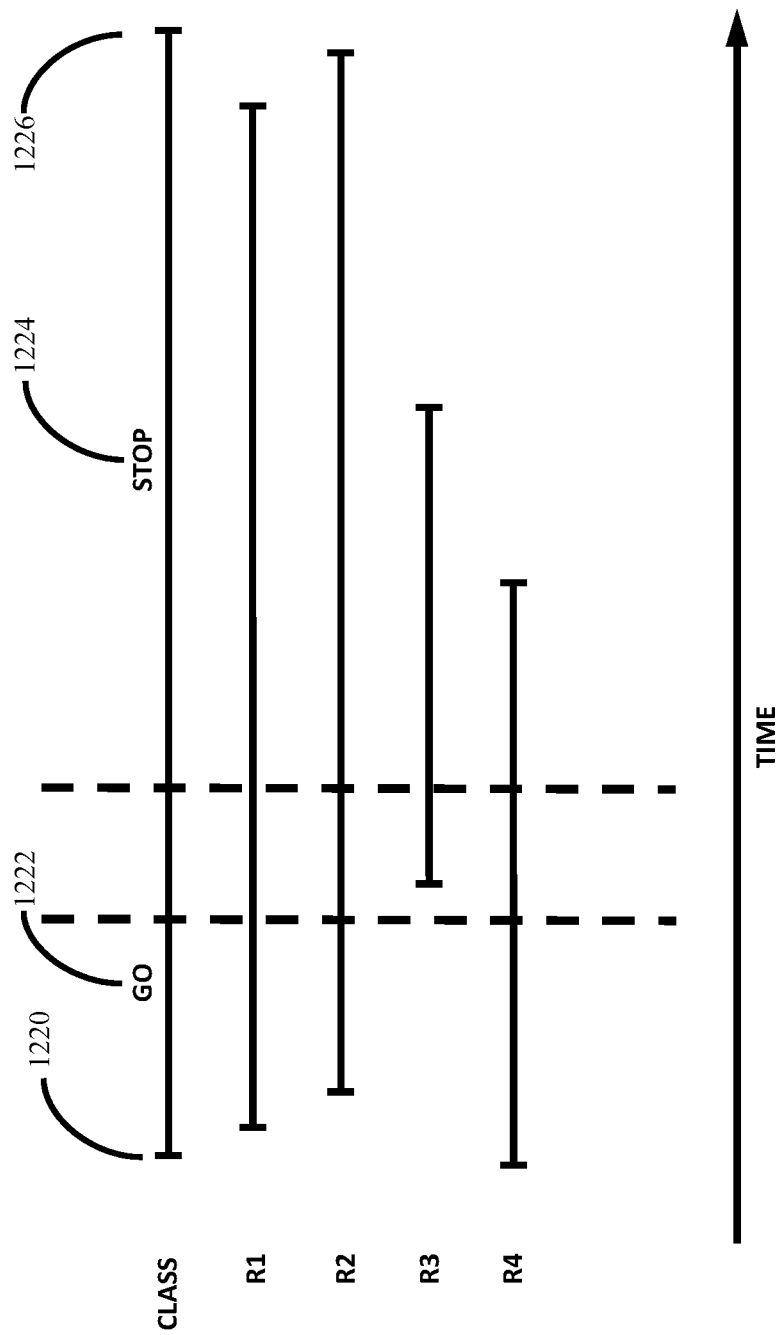
FIG. 12 is a chart showing an exemplary method for synchronizing data among users participating in the same live or on-demand cycling class, in accordance with an embodiment of the present disclosure.

Referring to FIGS. 10-11, the system may be configured to feed synchronized live and/or archived video content and live and/or archived sensor data to users over a digital asset distribution platform as disclosed herein. In various exemplary embodiments, the networked exercise system may be configured with a plurality of user bikes 1100 in communication with a video chat platform 1102, a distribution platform 1104 (such as the systems disclosed in FIGS. 1-7) that receives audio, video and other content from one or more content providers or hosts 1106. The user bikes 1100 may also be in communication with various other networks and servers. For example, the user bikes 1100 may exchange sensor and performance data and/or signaling with various databases 1108, including historical or "ghost bike" data. The distribution platform 1104 and/or an application server 1110 (e.g., an outlet server or a merchant server as previously described herein) may provide signals via the network to control the collection, storage, and management of data across the system.

One challenge for the use of comparative data from live and/or historical sources is synchronization, since some users may start riding prior to the start of the actual class, while others may join after the class has started. In order to provide accurate data regarding class performance for the leaderboard, including archived performance data, each class may have a specific "go" or start signal that serves as the starting time point for the data comparison. Archived performance data may be calibrated to the same "go" signal as live participant data, allowing for comparative data to be presented through a leaderboard or other display through the end of the class. A "stop" signal at the end of the class marks the end time point for the performance comparison for both live and archived performance data. If a rider joins the class after the "go" signal, their data can be synched correctly starting at the time they join the ride.

FIG. 11 shows various events relative to time, which is increasing from left to right on the scale at the bottom. The timeline for the class itself, whether live or archived, is shown at the top, with timelines for four different riders below it. The video being delivered for a live or archived class may begin before the actual class starts at the video start point 1220. The GO signal point 1222 indicates the start of the class or the class's comparison period, the STOP signal point 1224 indicates the end of the class or the end of the class's comparison period, and the end video point 1126 indicates the end of the video stream. For Riders 1, 2, and 4, who all start riding before the GO signal point, the GO signal serves as their starting time point for class performance metrics. For Rider 3, the point in time when they actually start will serve as their starting time point for class performance metrics. For Riders 1, 2, and 3 who continued past the STOP signal point, their end point for class performance metrics will be the STOP signal point, while the end point for Rider 4 will be the time when they actually stopped riding.

Using such a system, live and past performance (ghost bike) data for the user or other participants can be provided during a class in a range of numerical and graphical formats for comparison and competition. Live and past performance data or target performance data for the user can also be displayed simultaneously to allow users to compare their performance to a benchmark in real time during or after a class. In various exemplary embodiments, the system may also allow users to establish handicapping systems to equalize the competition among different users or user groups allowing for broad based competitions.

Figure 13:
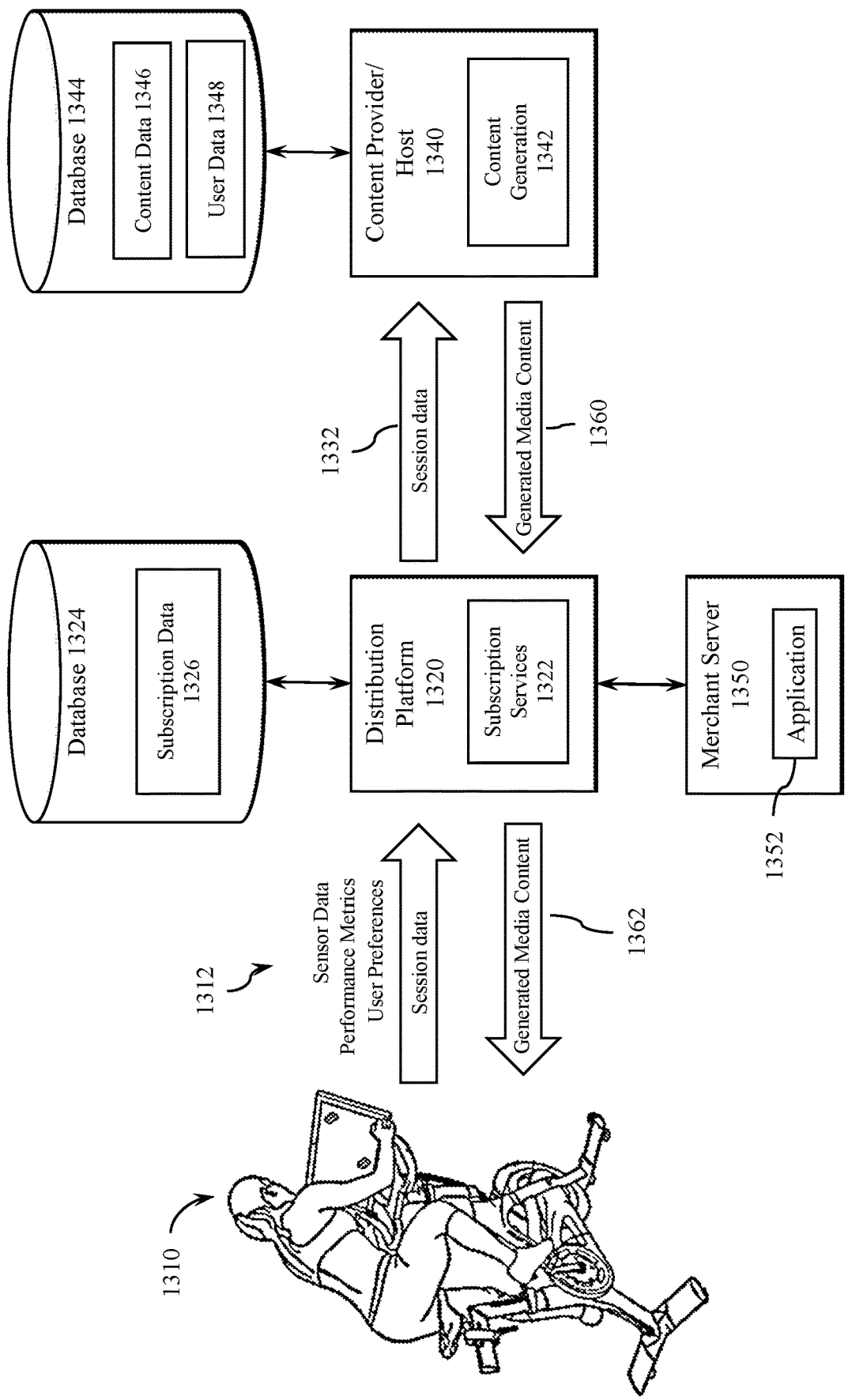
FIG. 13 is an example computing environment for distribution of computer generated media content, in accordance with an embodiment of the present disclosure.
Figure 14:
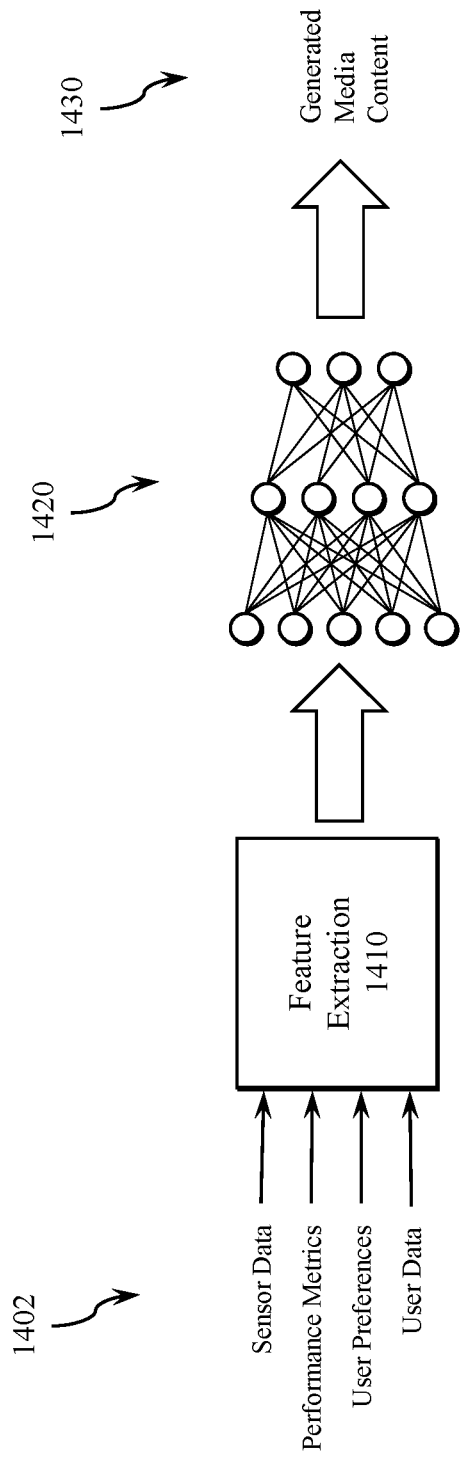
FIG. 14 is an example content generation process in accordance with an embodiment of the present disclosure.

In various embodiments, the system may use information provided by the local system to generate new media content in real time. The information may include sensor data, performance metrics of the user and/or class, personal preferences of the user (e.g., music choices), and other data. For example, user selection and/or feedback about a particular music choice may be used to generate new music in a similar style. Referring to FIGS. 13 and 14, embodiments of content creation and distribution systems and methods will now be described.

Referring to FIG. 13, a local system 1310 includes a user operating an exercise apparatus that includes one or more sensors, a processing system that generates one or more performance metrics and/or user preference information. During exercise, the local system 1310 transmits session data 1312 to the distribution platform 1320. In various embodiments, the session data 1312 may include sensor data (e.g., resistance, cadence, user heartrate), performance metrics (e.g., speed, distance, position on leaderboard), and/or user preference information (e.g., favorite music, workout preferences). A subscription services module 1322 verifies that an active subscription for the local system 1310 (user and application) is identified in the subscription data 1326 of the database 1324 and forwards the session data 1312 for content creation. In one embodiment, the session data 1312 is provided to a content provider/host system 1340, which includes content generation module 1342. In some embodiments, the merchant server 1350 running an application 1352 (e.g., a workout application) may receive the session data 1312 from the local system and add additional session data that is tracked or stored by the application 1352.

The content provider/host 1340 uses received session data 1332 to generate new digital media content, such as music or video content. The content generation module 1342 may use stored content data 1346 and user data 1348 (e.g., information on previous content generated for user) to generate new media content. The generated media content 1360 is returned to the distribution platform 1320 and provided to the local system as generated media content 1362. The generated media content 1362 may include a mixture of both generated media content and preexisting media content. For example, a video of a class instructor and audio of the class instructor's spoken instructions may be mixed with computer generated music.

Referring to FIG. 14, an embodiment of media content generation will now be described. The content generation module 1342 receives a stream of session data 1402 which may be used to generate media content in real time for streaming back to the local system. In one embodiment, the session data 1402 is provided to a feature extraction module 1410 which extracts data characteristics used to generate the media content. The generated features are provided to a content generation system, which may include a trained neural network configured to receive the generated features and output the generated music content 1430.

In operation, a media content creator may establish a channel through the distribution platform as a content creator. The media generation system may use input from the local system to create music and video creating an artificial reality for the exercise experience. This artificial reality may be mixed with content from a fitness instructor including audio from the fitness instructor, video from the fitness instructor, leaderboard information, etc. The media is dynamically generated and fed back to the channel for distribution to the local system.

In some embodiments, the generated media content allows for a personalized content package that is controlled by content creators. The distribution platform can separately track and manage the content, including artificially created content. The generated content can also change dynamically based on leaderboard information, data from other users, data from the instructor and other sources during the exercise session. In some embodiments, a content creator composes music through an artificial intelligence system that receives data such as speed, resistance and heartbeat from the user and generates media content corresponding to the exercise session. For example, the speed of a song in beats per minute can change in response to the user's pedal cadence. Video content can be modified in a similar manner.

In some embodiments, the user can select content from different services, and the distribution platform can seamlessness mix the content together for distribution to the local system. For example, a user can initiate a scenic ride with stock video, while music is generated dynamically based on data from the exercise session.

It will be appreciated that the content generation and distribution system disclosed herein may be used for other applications besides exercise sessions. For example, a patient may subscribe to a channel offering content for physical therapy, with access to a sequence of content (e.g., stages of physical recovery) managed through subscriptions. The distribution system may match the user to a content creator and/or make recommendations. The subscription services disclosed herein can facilitate a therapist/patient relationship, allowing the content provider (e.g., doctor or therapist) to track progress and use, including sensor feedback, camera feedback, etc. In another example, the content generation and distribution system may be used in an educational environment, providing instruction to the user in a controlled sequence of videos.

In various exemplary embodiments, the system may include a unique identifier on each bike to allow the system or user to track metrics on bike. This information could be used to user identification, or for maintenance, location, etc. In various exemplary embodiments, the system may also be configured to provide for closed classes. This would allow for a private instructor to work with an individual or small group, or for a group of users to ride together with or without an instructor.

In various exemplary embodiments, users can log in and/or access the system and account information via any appropriate communication technology including without limitation NFC, Bluetooth, WAN, etc. Users can also be provided with a cardkey, FOB, or other device or the stationary bike can be provided with facial recognition or voice recognition technology that automatically logs the user in and accesses their account information. Users can login from their home stationary bike or from any other bike that can access the system. Thus, while traveling a user can still access their complete account history, all content, and all features from any networked stationary bike such as at a hotel, a gym, or a cycling studio in a different location.

In various exemplary embodiments, a mobile application may allow users on non-networked stationary bikes to access the system via a mobile digital device such as a tablet computer or mobile phone and access content, live streams, and other system features. The mobile device could access the system via any appropriate network using a dedicated application or browser.

In various exemplary embodiments, one or more secondary display screens may be used by the system to display content for the exercise class. Using a device such as CHROMECAST or a similar integrated device to enable it to display content provided by the system through the user interface, a secondary display screen may be used to display content for the exercise class or other content provided by the system. The user interface could automatically detect the availability of such an enabled device and allow the user to select the display screen for particular content.

While the above description contains many specifics, these specifics should not be construed as limitations on the scope of the disclosure, but merely as exemplifications of the disclosed embodiments. Those skilled in the art will envision many other possible variations that fall within the scope and spirit of the disclosure. For example, although an exercise apparatus is illustrated it will be appreciated that the disclosed apparatus is one of many possible end-user platforms, and that the exercise bike is an example of one of many possible exercise equipment options. In various embodiments, various data inputs from a device or set of connected devices may include, but are not limited to, speed, resistance, heart rate, location temperature, location (on the map), location light/dark, as well as known history about the end user (e.g., likes and dislikes, such as music genre likes and artist preferences. Such data may play a function in customizing the content served by the system to the end user in real time or close to real time rendering, may it be pre-packaged on-demand content recommendation or the actual rendering or modification of content itself in response to such input. All such content and functionality may fit into a channel subscription of the digital content distribution systems and methods disclosed herein.

What is claimed is:

1. A media distribution system comprising:
a database storing information relating to media assets, application servers, content providers and end-users;
a platform server operable to facilitate distribution of media assets from the content providers to the application servers and end-user devices, the platform server configured to:
maintain content restriction data relating to the stored media assets, the content restriction data including access parameters received from an associated content provider;
generate a plurality of channels, each channel having channel characteristics associated with an application server and/or content provider and defining at least one media asset;
process a subscription request from an end-user for one of the plurality of channels, wherein a subscription is granted to the end-user satisfies the content restriction data and channel characteristics;
deliver channel media assets to the end-users in accordance with the subscription,
wherein the channel media assets include content associated with an exercise session performed by the end-users using exercise apparatuses associated with the end-users; and
receive performance data from the exercise apparatuses, wherein the performance data is based on exercise activity of the end-users during streaming of the exercise session via the exercise apparatuses and is captured by the exercise apparatuses.

2. A system, comprising:
a database storing exercise content and data associated with a content provider and an application provider; and
a platform server operable to facilitate delivery of the exercise content to an exercise apparatus, the platform server configured to:
receive performance data, from the exercise apparatus, which is based on movement of a portion of the exercise apparatus during an exercise class;
forward the performance data to the content provider;
receive updated content associated with the exercise class from the content provider; and
deliver the updated content to the exercise apparatus, wherein the updated content associated with the exercise class includes:
computer-generated, or computer-modified, media content generated from the performance data through a neural network, or
a combination of pre-existing content and computer-generated or computer modified media content generated and combined from the performance data through a neural network.

3. The system of claim 2, wherein the performance data includes sensor data, user performance metrics, or user preference data for a user of the exercise apparatus.

4. The system of claim 2, wherein the exercise content includes computer-generated content comprising computer generated music or computer-generated video;
wherein the computer-generated content is generated in real-time during transmission of the exercise class; and
wherein the computer-generated content changes in response to changes in the performance data.

5. The system of claim 4, wherein the performance data includes cadence data, speed data, or heart rate data.

6. The system of claim 2, wherein the exercise content of the content provider includes exercise class content including audio cues from an exercise instructor, video content of the exercise instructor, or scenery.

7. The system of claim 2, wherein the updated content associated with the exercise class is delivered to the exercise apparatus by the application provider through an application facilitating the exercise class running on an application server; and wherein the application facilitating the exercise class generates session content for delivery to the exercise apparatus.

8. The system of claim 2, wherein the platform server is further operable to:
maintain content restriction data relating to the stored exercise content, the content restriction data including access parameters received from an associated content provider;
generate a plurality of channels, each channel having channel characteristics associated with an application server and/or content provider and defining at least one media asset;
process a subscription request from an end user for one of the plurality of channels,
wherein a subscription is granted to the end-user satisfies the content restriction data and channel characteristics; and
deliver channel media assets to the exercise apparatus in accordance with the subscription.

9. The system of claim 8, wherein the platform server is further configured to process a payment from a user associated with the exercise apparatus in accordance with the subscription request; and
allocate a portion of the payment among an account associated with the application server and the content provider, in accordance with the access parameters, the channel characteristics, or the subscription.

10. The system of claim 8, wherein the database includes data organized by a subscription model, including multiple subscription plans defined by content providers or application servers that are produced, syndicated, and administered by the platform server as subscription media channels.

11. The system of claim 8, further comprising:
a crypto-currency engine operable to generate, sell, trade, and administer crypto-currency tokens;
wherein the crypto-currency tokens have value recognized by the platform server;
wherein the platform server is further configured to accept one or more of the crypto-currency tokens as payment for the subscription.

12. A method, comprising:
receiving performance data from an exercise apparatus during an exercise class,
wherein the exercise apparatus presents exercise content to a user of the exercise apparatus during the exercise class;
generating updated exercise content based on the performance data via a neural network; and
delivering the updated content to the exercise apparatus.

13. The method of claim 12, wherein the updated exercise content includes computer-generated or computer-modified media content generated from the performance data via the neural network.

14. The method of claim 12, wherein the updated exercise content includes a combination of pre-existing content and computer-generated or computer-modified media content generated and combined from the performance data via the neural network.

15. The method of claim 12, further comprising:
forwarding the performance data to a content provider; and
receiving the updated exercise content from the content provider.

16. The method of claim 12, wherein the performance data is based on movement of a portion of the exercise apparatus during the exercise class.

17. The method of claim 12, wherein the performance data includes sensor data, user performance metrics, or user preference data for the user of the exercise apparatus.

18. The method of claim 12, wherein the performance data includes cadence data, speed data, or heart rate data.

19. The method of claim 12, wherein the updated exercise content includes computer-generated content comprising computer generated music or computer-generated video;
wherein the computer-generated content is generated in real-time during the exercise class; and
wherein the computer-generated content changes in response to changes in the performance data.

20. The method of claim 12, wherein the exercise content includes exercise class content having audio cues from an exercise instructor and video content of the exercise instructor.

* * * * *